(12) United States Patent
Yang et al.

(10) Patent No.: US 10,562,976 B2
(45) Date of Patent: Feb. 18, 2020

(54) IMMUNOCONJUGATE AND USES THEREOF

(71) Applicant: Academia Sinica, Taipei (TW)

(72) Inventors: An-Suei Yang, Emeryville, CA (US); Wei-Ying Kuo, Taipei (TW); Hung-Ju Hsu, Taipei (TW); Hong-Sen Chen, Taipei (TW); Yu-Chi Chou, Taipei (TW); Yueh-Liang Tsou, Taipei (TW); Hung-Pin Peng, Taipei (TW); Jhih-Wei Jian, Taipei (TW); Chung-Ming Yu, Taipei (TW); Yi-Kai Chiu, Taipei (TW); Ing-Chein Chen, Taipei (TW); Chao-Ping Tung, Taipei (TW); Michael Hsiao, Taipei (TW); Hwei-Jiung Wang, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 16/166,220

(22) Filed: Oct. 22, 2018

(65) Prior Publication Data
US 2019/0040151 A1    Feb. 7, 2019

Related U.S. Application Data

(63) Continuation-in-part of application No. 15/619,835, filed on Jun. 12, 2017.

(60) Provisional application No. 62/348,860, filed on Jun. 11, 2016.

(51) Int. Cl.
*A61K 39/00* (2006.01)
*A61K 39/38* (2006.01)
*A61K 39/395* (2006.01)
*C07K 16/30* (2006.01)
*A61K 47/68* (2017.01)
*A61P 35/00* (2006.01)
*C07K 16/32* (2006.01)

(52) U.S. Cl.
CPC .... *C07K 16/3015* (2013.01); *A61K 39/39558* (2013.01); *A61K 47/6829* (2017.08); *A61K 47/6855* (2017.08); *A61K 47/6889* (2017.08); *A61P 35/00* (2018.01); *C07K 16/32* (2013.01); *A61K 2039/505* (2013.01); *C07K 2317/622* (2013.01); *C07K 2317/73* (2013.01); *C07K 2317/77* (2013.01); *C07K 2317/92* (2013.01); *C07K 2317/94* (2013.01)

(58) Field of Classification Search
CPC .............................. A61K 39/00; A61K 39/395
USPC .......... 424/130.1, 133.1, 178.1, 184.1, 185.1
See application file for complete search history.

*Primary Examiner* — Rodney P Swartz

(57) ABSTRACT

Disclosed herein is an immunoconjugate comprising an antibody, a functional motif, and a linker connecting the functional motif to the antibody. According to embodiments of the present disclosure, the antibody may recognize tumor-associated antigens (TAAs), and serves as a targeting module for delivering the functional motif connected therewith to the tumor cells thereby inhibiting tumor growth or detecting the distribution of tumor cells. Also disclosed herein are methods of treating cancers and methods of diagnosing cancers by use of the present immunoconjugate.

13 Claims, 10 Drawing Sheets
(2 of 10 Drawing Sheet(s) Filed in Color)
Specification includes a Sequence Listing.

E

F

A

B

B

C

B

```
                         SEQUENCE LISTING

<160> NUMBER OF SEQ ID NOS: 32

<210> SEQ ID NO 1
<211> LENGTH: 7
<212> TYPE: PRT
<213> ORGANISM: Artificial Sequence
<220> FEATURE:
<223> OTHER INFORMATION: synthesized-GH2-20 HC-CDR1

<400> SEQUENCE: 1

Leu Thr Ile Asn Asp Tyr Gly
1               5

<210> SEQ ID NO 2
<211> LENGTH: 10
<212> TYPE: PRT
<213> ORGANISM: Artificial Sequence
<220> FEATURE:
<223> OTHER INFORMATION: synthesized-GH2-20 HC-CDR2

<400> SEQUENCE: 2

Ser Ile Gly Pro Ser Gly Gly Phe Thr Ser
1               5                   10

<210> SEQ ID NO 3
<211> LENGTH: 7
<212> TYPE: PRT
<213> ORGANISM: Artificial Sequence
<220> FEATURE:
<223> OTHER INFORMATION: synthesized-GH2-20 HC-CDR3

<400> SEQUENCE: 3

Val Ile Tyr Trp Gly Phe Phe
1               5

<210> SEQ ID NO 4
<211> LENGTH: 5
<212> TYPE: PRT
<213> ORGANISM: Artificial Sequence
<220> FEATURE:
<223> OTHER INFORMATION: synthesized-GH2-20 LC-CDR2

<400> SEQUENCE: 4

Tyr Trp Thr Thr Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: synthesized-GH2-20 LC-CDR3

<400> SEQUENCE: 5

Gly Ser Asn Trp Pro Ile
1               5

<210> SEQ ID NO 6
<211> LENGTH: 7
<212> TYPE: PRT
<213> ORGANISM: Artificial Sequence
<220> FEATURE:
<223> OTHER INFORMATION: synthesized-GH2-61 HC-CDR1
```

<400> SEQUENCE: 6

Phe Thr Ile Asn Asn Trp Gly
1               5

<210> SEQ ID NO 7
<211> LENGTH: 10
<212> TYPE: PRT
<213> ORGANISM: Artificial Sequence
<220> FEATURE:
<223> OTHER INFORMATION: synthesized-GH2-61 HC-CDR2

<400> SEQUENCE: 7

Gly Ile Trp Pro Tyr Gly Gly Tyr Thr Tyr
1               5                   10

<210> SEQ ID NO 8
<211> LENGTH: 7
<212> TYPE: PRT
<213> ORGANISM: Artificial Sequence
<220> FEATURE:
<223> OTHER INFORMATION: synthesized-GH2-61 HC-CDR3

<400> SEQUENCE: 8

Tyr Asn His His Gly Gly Val
1               5

<210> SEQ ID NO 9
<211> LENGTH: 5
<212> TYPE: PRT
<213> ORGANISM: Artificial Sequence
<220> FEATURE:
<223> OTHER INFORMATION: synthesized-GH2-61 LC-CDR2

<400> SEQUENCE: 9

Ser Trp Ser Thr Ser
1               5

<210> SEQ ID NO 10
<211> LENGTH: 6
<212> TYPE: PRT
<213> ORGANISM: Artificial Sequence
<220> FEATURE:
<223> OTHER INFORMATION: synthesized-GH2-61 LC-CDR3

<400> SEQUENCE: 10

Tyr Gly Gly Trp Pro Ile
1               5

<210> SEQ ID NO 11
<211> LENGTH: 7
<212> TYPE: PRT
<213> ORGANISM: Artificial Sequence
<220> FEATURE:
<223> OTHER INFORMATION: synthesized-GH2-75 HC-CDR1

<400> SEQUENCE: 11

Ser Thr Ile Gly Asn Ser Gly
1               5

<210> SEQ ID NO 12
<211> LENGTH: 10
<212> TYPE: PRT
<213> ORGANISM: Artificial Sequence
<220> FEATURE:
<223> OTHER INFORMATION: synthesized-GH2-75 HC-CDR2

```
<400> SEQUENCE: 12

Tyr Ile Gly Pro Tyr Gly Gly Tyr Thr Ser
1               5                   10

<210> SEQ ID NO 13
<211> LENGTH: 7
<212> TYPE: PRT
<213> ORGANISM: Artificial Sequence
<220> FEATURE:
<223> OTHER INFORMATION: synthesized-GH2-75 HC-CDR3

<400> SEQUENCE: 13

Asp Asp Tyr His Trp Asp Gly
1               5

<210> SEQ ID NO 14
<211> LENGTH: 6
<212> TYPE: PRT
<213> ORGANISM: Artificial Sequence
<220> FEATURE:
<223> OTHER INFORMATION: synthesized-GH2-75 LC-CDR3

<400> SEQUENCE: 14

Tyr Tyr Asn Trp Pro Val
1               5

<210> SEQ ID NO 15
<211> LENGTH: 120
<212> TYPE: PRT
<213> ORGANISM: Artificial Sequence
<220> FEATURE:
<223> OTHER INFORMATION: synthesized-GH2-20 heavy chain

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Ile Asn Asp Tyr
            20                  25                  30

Gly Ile His Trp Val Arg Gln Ala Pro Gly Lys Gly Leu Glu Trp Val
        35                  40                  45

Ala Ser Ile Gly Pro Ser Gly Gly Phe Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Ile Tyr Trp Gly Phe Phe Met Asp Tyr Trp Gly Gln
            100                 105                 110

Gly Thr Leu Val Thr Val Ser Ser
        115                 120

<210> SEQ ID NO 16
<211> LENGTH: 108
<212> TYPE: PRT
<213> ORGANISM: Artificial Sequence
<220> FEATURE:
<223> OTHER INFORMATION: synthesized-GH2-20 light chain

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Asn
```

```
                    20                  25                  30

Val Ala Trp Tyr Gln Gln Lys Pro Gly Lys Ala Pro Lys Leu Leu Ile
                35                  40                  45

Tyr Trp Thr Thr Tyr Leu Tyr Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ser Asn Trp Pro Ile
                85                  90                  95

Thr Phe Gly Gln Gly Thr Lys Val Glu Ile Lys Arg
                100                 105
```

<210> SEQ ID NO 17
<211> LENGTH: 120
<212> TYPE: PRT
<213> ORGANISM: Artificial Sequence
<220> FEATURE:
<223> OTHER INFORMATION: synthesized-GH2-61 heavy chain

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Asn Trp
                20                  25                  30

Gly Ile His Trp Val Arg Gln Ala Pro Gly Lys Gly Leu Glu Trp Val
                35                  40                  45

Ala Gly Ile Trp Pro Tyr Gly Gly Tyr Thr Tyr Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Tyr Asn His His Gly Gly Val Met Asp Tyr Trp Gly Gln
                100                 105                 110

Gly Thr Leu Val Thr Val Ser Ser
        115                 120
```

<210> SEQ ID NO 18
<211> LENGTH: 108
<212> TYPE: PRT
<213> ORGANISM: Artificial Sequence
<220> FEATURE:
<223> OTHER INFORMATION: synthesized-GH2-61 light chain

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Asn
                20                  25                  30

Val Ala Trp Tyr Gln Gln Lys Pro Gly Lys Ala Pro Lys Leu Leu Ile
                35                  40                  45

Ser Trp Ser Thr Ser Leu Tyr Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Gly Trp Pro Ile
                85                  90                  95
```

```
Thr Phe Gly Gln Gly Thr Lys Val Glu Ile Lys Arg
            100                 105
```

<210> SEQ ID NO 19
<211> LENGTH: 120
<212> TYPE: PRT
<213> ORGANISM: Artificial Sequence
<220> FEATURE:
<223> OTHER INFORMATION: synthesized-GH2-75 heavy chain

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Ile Gly Asn Ser
            20                  25                  30

Gly Ile His Trp Val Arg Gln Ala Pro Gly Lys Gly Leu Glu Trp Val
        35                  40                  45

Ala Tyr Ile Gly Pro Tyr Gly Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asp Asp Tyr His Trp Asp Gly Met Asp Tyr Trp Gly Gln
            100                 105                 110

Gly Thr Leu Val Thr Val Ser Ser
        115                 120
```

<210> SEQ ID NO 20
<211> LENGTH: 103
<212> TYPE: PRT
<213> ORGANISM: Artificial Sequence
<220> FEATURE:
<223> OTHER INFORMATION: synthesized-GH2-75 light chain

<400> SEQUENCE: 20

```
Asp Ile Gln Met Thr Gln Ser Pro Ser Ser Leu Ser Ala Ser Val Gly
1               5                   10                  15

Asp Arg Val Ile Ile Thr Cys Arg Ala Ser Gln Asp Val Ser Gly Tyr
            20                  25                  30

Val Ala Trp Tyr Gln Gln Lys Pro Gly Lys Ala Pro Lys Leu Leu Ile
        35                  40                  45

Tyr Ser Ser Gly Val Pro Ser Arg Phe Ser Gly Ser Gly Ser Gly Thr
    50                  55                  60

Asp Phe Thr Leu Thr Ile Ser Ser Leu Gln Pro Glu Asp Phe Ala Thr
65                  70                  75                  80

Tyr Tyr Cys Gln Gln Tyr Tyr Asn Trp Pro Val Thr Phe Gly Gln Gly
                85                  90                  95

Thr Lys Val Glu Ile Lys Arg
            100
```

<210> SEQ ID NO 21
<211> LENGTH: 4
<212> TYPE: PRT
<213> ORGANISM: Artificial Sequence
<220> FEATURE:
<223> OTHER INFORMATION: synthesized-ER retention peptide

<400> SEQUENCE: 21

Lys Asp Glu Leu

<210> SEQ ID NO 22
<211> LENGTH: 9
<212> TYPE: PRT
<213> ORGANISM: Artificial Sequence
<220> FEATURE:
<223> OTHER INFORMATION: synthesized-linking sequence

<400> SEQUENCE: 22

```
Ala Ser Ala Ala Gly Gly Ser Gly Thr
1               5
```

<210> SEQ ID NO 23
<211> LENGTH: 138
<212> TYPE: PRT
<213> ORGANISM: Artificial Sequence
<220> FEATURE:
<223> OTHER INFORMATION: synthesized-adaptor

<400> SEQUENCE: 23

```
Tyr Asn Lys Asp Gln Gln Ser Ala Phe Tyr Glu Ile Leu Asn Met Pro
1               5                   10                  15

Asn Leu Asn Glu Glu Gln Arg Asn Gly Phe Ile Gln Ser Leu Lys Asp
            20                  25                  30

Asp Pro Ser Gln Ser Thr Asn Val Leu Gly Glu Ala Lys Lys Leu Asn
        35                  40                  45

Glu Ser Gln Ala Pro Lys Ala Asp Asn Gly Gly Ser Gly Gly Gly
    50                  55                  60

Ser Gly Gly Gly Ser Gly Gly Ser Gly Ser Glu Val Thr Ile
65                  70                  75                  80

Lys Val Asn Leu Ile Phe Ala Asp Gly Lys Ile Gln Thr Ala Glu Phe
                85                  90                  95

Lys Gly Thr Phe Glu Glu Ala Thr Ala Glu Ala Tyr Arg Tyr Ala Ala
            100                 105                 110

Leu Leu Ala Lys Val Asn Gly Glu Tyr Thr Ala Asp Leu Glu Asp Gly
        115                 120                 125

Gly Asn His Met Asn Ile Lys Phe Ala Gly
    130                 135
```

<210> SEQ ID NO 24
<211> LENGTH: 41
<212> TYPE: DNA
<213> ORGANISM: Artificial Sequence
<220> FEATURE:
<223> OTHER INFORMATION: synthesized-F1 primer

<400> SEQUENCE: 24
aatggactat catatgctta ccgtaacttg aaagtatttc g                41

<210> SEQ ID NO 25
<211> LENGTH: 44
<212> TYPE: PRT
<213> ORGANISM: Artificial Sequence
<220> FEATURE:
<223> OTHER INFORMATION: synthesized-R1 primer

<400> SEQUENCE: 25

```
Cys Thr Thr Thr Ala Gly Thr Thr Gly Thr Ala Thr Gly Thr Cys
1               5                   10                  15

Thr Gly Thr Thr Gly Cys Thr Ala Thr Thr Ala Thr Gly Thr Cys Thr
            20                  25                  30
```

Ala Cys Thr Ala Thr Thr Cys Thr Thr Thr Cys Cys
         35                  40

<210> SEQ ID NO 26
<211> LENGTH: 23
<212> TYPE: DNA
<213> ORGANISM: Artificial Sequence
<220> FEATURE:
<223> OTHER INFORMATION: synthesized-F2 primer

<400> SEQUENCE: 26
cttgtggaaa ggacgaaaca ccg                                       23

<210> SEQ ID NO 27
<211> LENGTH: 25
<212> TYPE: DNA
<213> ORGANISM: Artificial Sequence
<220> FEATURE:
<223> OTHER INFORMATION: synthesized-R2 primer

<400> SEQUENCE: 27
tctactattc tttcccctgc actgt                                     25

<210> SEQ ID NO 28
<211> LENGTH: 20
<212> TYPE: DNA
<213> ORGANISM: Artificial Sequence
<220> FEATURE:
<223> OTHER INFORMATION: synthesized-control sgRNA

<400> SEQUENCE: 28
gcgaggtatt cggctccgcg                                           20

<210> SEQ ID NO 29
<211> LENGTH: 20
<212> TYPE: DNA
<213> ORGANISM: Artificial Sequence
<220> FEATURE:
<223> OTHER INFORMATION: synthesized-KDELR2 sgRNA

<400> SEQUENCE: 29
cgccggccac cacagcaatg                                           20

<210> SEQ ID NO 30
<211> LENGTH: 20
<212> TYPE: DNA
<213> ORGANISM: Artificial Sequence
<220> FEATURE:
<223> OTHER INFORMATION: synthesized-FURIN sgRNA

<400> SEQUENCE: 30
tcggggacta ttaccacttc                                           20

<210> SEQ ID NO 31
<211> LENGTH: 344
<212> TYPE: PRT
<213> ORGANISM: Artificial Sequence
<220> FEATURE:
<223> OTHER INFORMATION: synthesized-PE38KDEL

<400> SEQUENCE: 31

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
            35                  40                  45

Ala Arg Leu Ser Trp Asn Gln Val Asp Gln Val Ile Arg Asn Ala Leu
     50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Ala Glu Ser Glu
                85                  90                  95

Arg Phe Val Arg Gln Gly Thr Gly Asn Asp Glu Ala Gly Ala Ala Asn
            100                 105                 110

Gly Pro Ala Asp Ser Gly Asp Ala Leu Leu Glu Arg Asn Tyr Pro Thr
        115                 120                 125

Gly Ala Glu Phe Leu Gly Asp Gly Gly Asp Val Ser Phe Ser Thr Arg
    130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
            180                 185                 190

Asp Leu Asp Ala Ile Trp Arg Gly Phe Tyr Ile Ala Gly Asp Pro Ala
        195                 200                 205

Leu Ala Tyr Gly Tyr Ala Gln Asp Gln Glu Pro Asp Ala Arg Gly Arg
    210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Gly Gly Arg Leu Glu Thr Ile Leu
        275                 280                 285

Gly Trp Pro Leu Ala Glu Arg Thr Val Val Ile Pro Ser Ala Ile Pro
    290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Lys Asp Glu Leu
            340

<210> SEQ ID NO 32
<211> LENGTH: 360
<212> TYPE: PRT
<213> ORGANISM: Artificial Sequence
<220> FEATURE:
<223> OTHER INFORMATION: synthesized-PE38

<400> SEQUENCE: 32

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
                20                  25                  30

Glu Gln Cys Gly Tyr Pro Val Gln Arg Leu Val Ala Leu Tyr Leu Ala
            35                  40                  45

```
Ala Arg Leu Ser Trp Asn Gln Val Asp Gln Val Ile Arg Asn Ala Leu
    50              55              60
Ala Ser Pro Gly Ser Gly Gly Asp Leu Gly Glu Ala Ile Arg Glu Gln
65              70              75              80
Pro Glu Gln Ala Arg Leu Ala Leu Thr Leu Ala Ala Glu Ser Glu
                85              90              95
Arg Phe Val Arg Gln Gly Thr Gly Asn Asp Glu Ala Gly Ala Ala Asn
                100             105             110
Ala Asp Val Val Ser Leu Thr Cys Pro Val Ala Ala Gly Glu Cys Ala
            115             120             125
Gly Pro Ala Asp Ser Gly Asp Ala Leu Leu Glu Arg Asn Tyr Pro Thr
    130             135             140
Gly Ala Glu Phe Leu Gly Asp Gly Gly Asp Val Ser Phe Ser Thr Arg
145             150             155             160
Gly Thr Gln Asn Trp Thr Val Glu Arg Leu Leu Gln Ala His Arg Gln
                165             170             175
Leu Glu Glu Arg Gly Tyr Val Phe Val Gly Tyr His Gly Thr Phe Leu
                180             185             190
Glu Ala Ala Gln Ser Ile Val Phe Gly Gly Val Arg Ala Arg Ser Gln
            195             200             205
Asp Leu Asp Ala Ile Trp Arg Gly Phe Tyr Ile Ala Gly Asp Pro Ala
    210             215             220
Leu Ala Tyr Gly Tyr Ala Gln Asp Gln Glu Pro Asp Ala Arg Gly Arg
225             230             235             240
Ile Arg Asn Gly Ala Leu Leu Arg Val Tyr Val Pro Arg Ser Ser Leu
                245             250             255
Pro Gly Phe Tyr Arg Thr Ser Leu Thr Leu Ala Ala Pro Glu Ala Ala
                260             265             270
Gly Glu Val Glu Arg Leu Ile Gly His Pro Leu Pro Leu Arg Leu Asp
            275             280             285
Ala Ile Thr Gly Pro Glu Glu Gly Gly Arg Leu Glu Thr Ile Leu
    290             295             300
Gly Trp Pro Leu Ala Glu Arg Thr Val Val Ile Pro Ser Ala Ile Pro
305             310             315             320
Thr Asp Pro Arg Asn Val Gly Gly Asp Leu Asp Pro Ser Ser Ile Pro
                325             330             335
Asp Lys Glu Gln Ala Ile Ser Ala Leu Pro Asp Tyr Ala Ser Gln Pro
                340             345             350
Gly Lys Pro Pro Arg Glu Asp Leu
    355             360
```

IMMUNOCONJUGATE AND USES THEREOF

CROSS-REFERENCE TO RELATED APPLICATION

This application is a continuation-in-part of U.S. application Ser. No. 15/619,835, filed Jun. 12, 2017, which claims the benefit of U.S. Provisional Application No. 62/348,860, filed Jun. 11, 2016, the contents of said application are incorporated herein by reference in its entirety.

STATEMENT REGARDING PRIOR DISCLOSURES BY THE INVENTOR OR A JOINT INVENTOR UNDER 37 C.F.R. 1.77(B)(6)

Most of the subject matter of the invention described in the present application was published by the inventors, An-Suei Yang, Wei-Ping Kuo, Hung-Ju Hsu, Hong-Sen Chen, Yu-Chi Chou, Yueh-Liang Tsou, Hung-Pin Peng, Jhih-Wei Jian, Chung-Ming Yu, Yi-Kai Chiu, Ing-Chien Chen, Chao-Ping Tung, Michael Hsiao, and Hwei-Jiung Wang in a poster titled "New technological platform for novel antibody drug conjugate development." The poster was published on Jun. 1, 2018. The publication was made by and/or originated from all member of the inventive entity of the present invention, and the entirety of this article is incorporated herein by reference. A copy of the poster is provided in a concurrently filed Information Disclosure Statement pursuant to the guidance of 78 Fed. Reg. 11076 (Feb. 14, 2013).

BACKGROUND OF THE INVENTION

1. Field of the Invention

The present disclosure in general relates to the field of cancer treatment and/or diagnosis. More particularly, the present disclosure relates to the treatment and/or diagnosis of cancers by use of immunoconjugates.

2. Description of Related Art

HER2-ECD (human epidermal growth factor receptor 2-extracellular domain) is a prominent therapeutic target validated for treating HER2-positive breast and gastric cancer. More than 600 clinical studies currently registered in ClinicalTrials.gov are related to HER2-positive cancers, and about a quarter of these studies are involved with antibody-based therapeutics/diagnostics targeting HER2-ECD. In addition to breast cancer and gastric cancer, HER2 over-expression has been found in other diverse cancers, suggesting that a substantial number of cancer patients could potentially be benefited from antibody therapeutics targeting HER2-ECD. Already, two HER2-ECD-targeting monoclonal antibodies have been used in treating cancers in humans: trastuzumab for HER2-positive breast, gastric and gastroesophageal junction cancer; pertuzumab for HER2-positive breast cancer in metastatic or neoadjuvant setting. In addition, trastuzumab emtansine (T-DM1), an antibody-drug conjugate (ADC) comprising trastuzumab conjugated through a non-reducible linker to the tubulin inhibitor emtansine (DM1), has been approved for treating HER2-positive metastatic breast cancer and shown overall survival benefit and favorable safety profile over long follow-up durations. However, a recent report on the international randomized GATZBY phase 2/3 trial indicates that trastuzumab emtansine is not superior to taxane in patients with previously treated HER2-positive advanced gastric cancer. While HER2-ECD remains a validated target in several ongoing and planned clinical gastric cancer studies, HER2-specific therapeutic options for treating advanced gastric cancer are still limited.

A general technological platform has been established to rapidly develop antibody-based immunoconjugates as therapeutics; this platform was used to develop ADC candidates targeting HER2-ECD on N87 cells, which are standard cell systems acting as HER2 over-expressing human gastric cancer cell line and xenograft model. The technological platform has two main components: phage-displayed synthetic antibody scFv (single chain variable domain) libraries and high throughput discovery technique of ADC candidates from the scFv libraries with adaptor-toxin fusion proteins as cytotoxic payloads. The synthetic antibody libraries were designed based on the antibody-protein interaction principles derived from computational and experimental analyses and built on a single human variable domain antibody germline framework (IGKV1-NL1*01/IGHV3-23*04) with high affinity to Protein A and Protein L, which bind to the variable domain framework heavy and light chain regions respectively without affecting the antigen binding sites of the scFvs. These synthetic antibody libraries have been demonstrated to be highly effective; hundreds of scFvs binding to HER2-ECD with high affinity and specificity on diverse epitopes have been discovered with phage display-based selection and screening. With high throughput measurements, the HER2-ECD-positive scFvs from the synthetic antibody libraries were tested as targeting modules of immunoconjugates by combining with the adaptor-toxin fusion proteins AL1-PE38KDEL and AL2-PE38KDEL for delivering PE38KDEL, a truncated form of *Pseudomonas* Exotoxin (PE) A subunit toxin, to N87 cells; the scFvs were non-covalently linked to PE38KDEL through the AL1 fragment with consecutive Protein A and Protein L separated by a polypeptide linker that enables the Protein A and Protein L binding to the framework regions of the scFv simultaneously with nano-molar affinity. Similarly, the AL2 fragment contains two consecutive AL1 modules separated by another polypeptide linker with length designed to promote two scFvs binding simultaneously to the AL2 fragment to mimic the bivalent antigen binding of IgG with 2 antigen binding domains in one immunoconjugate complex. The ADC discovery platform has been demonstrated to yield scFv candidates as targeting modules for immunoconjugates with potent cytotoxicity toward N87 cells.

In this work, three HER2-ECD-positive scFv candidates (GH2-20, GH2-61 and GH2-75) from the synthetic antibody libraries selected through the antibody-based immunoconjugate discovery platform with the highest potencies as targeting modules toward N87 cells were reformatted into human IgG1 antibodies and tested together with two positive control IgG1 antibodies (trastuzumab and H32, both are humanized murine anti-HER2-ECD antibodies) and one isotype negative control IgG1 antibody (nc) in three forms of immunoconjugates for efficacy measurements with in vitro N87 cultured cells and in vivo xenograft models. The scFvs were selected by the representative physicochemical properties: all the selected scFvs (GH2-20, GH2-61 and GH2-75) are among the most potent targeting modules in a large set of non-covalently linked immunotoxins with $IC_{50}$ for scFv-AL2-PE38KDEL <0.01 nM and $IC_{50}$ for scFv-AL1-PE38KDEL <0.1 nM. The epitopes of GH2-61 and GH2-75 are overlapped with that of the positive control antibody H32, for which the epitope has been identified on domain I of HER2-ECD as determined with negative stain electron microscopy. The epitope of GH2-20 does not overlap with that of H32, and indirect evidence suggests that its epitope was situated on domain IV of HER2-ECD but not overlap with trastuzumab's epitope, which is also situated on domain IV of HER2-ECD as determined with x-ray crystallography (PDB code: 1N8Z). GH2-61, GH2-20, H32 and trastuzumab IgG1 antibodies have similar on/off rates and nano-molar monovalent dissociation constants binding to HER2-ECD (measure with surface plasmon resonance shown in Table 2); the affinity of GH2-75 IgG1 to HER2-ECD is about one order of magnitude inferior in terms of the monovalent dissociation constant and the off rate binding to HER2-ECD (Table 2). The efficacies of these antibodies as the targeting modules for delivering diverse cytotoxic payloads to xenograft tumor models in vivo and to cultured cells in vitro were scrutinized with three forms of immunoconjugates in this work: (1) ADC in the form of IgG1-vc-MMAE (monomethyl auristatin E linked to the IgG1 via valine-citrulline dipeptide cathepsin-cleavable linker); (2) immunotoxin of a single polypeptide chain in the form of scFv-PE38KDEL fusion protein; and (3) immunotoxin in the form of IgG1-AL1-PE38KDEL, where the IgG1 is non-covalently linked to PE38KDEL through the adaptor-toxin fusion protein AL1-PE38KDEL. The differences in the cytotoxic payloads and linkers among the three forms of immunoconjugate were anticipated to result in different effects on the efficacies of the antibodies as the immunoconjugates' targeting modules.

The in vitro and in vivo efficacy/toxicity comparisons among the antibodies and the three forms of immunoconjugates informed the ADC candidate selection with different prospects on the candidate antibodies' potencies and off-target toxicities. The results in this work showed that two out of the three selected ADC candidates (GH2-61 and GH2-20) with potential for treating human HER2-positive gastric cancer were favorably supported in terms of completely eradicating the xenograft tumor at the end point of the treatment with the ADCs. The immunotoxins (scFv-PE38KDEL) also showed efficacies in inhibiting the progression of xenograft tumor by GH2-61 scFv, but the off-target toxicities to the xenograft models by the other scFv candidates were evident even at much lower dosage level in comparison with the corresponding ADCs. Nevertheless, the immunotoxins could be envisaged as a sensitive surrogate system for detecting potential off-target toxicity in vivo associated with the antibodies as the targeting modules in immunoconjugates. The non-covalently linked immunotoxins (IgGs-AL1-PE38KDEL) are much easier to prepare in comparison with the corresponding ADCs and are more tolerable in term of off-target toxicity in comparison with the corresponding scFv-PE38KDELs, and hence could be envisaged as a surrogate system to qualitatively inform the selection of IgG candidates for further ADC development in terms of efficacy and off-target toxicity. These findings supported the utility of the general ADC discovery platform on the basis of the synthetic antibody libraries and provided insights into the optimization of the therapeutic efficacies of the antibodies as targeting modules in ADCs.

The major treatments for cancer include surgery, radiation therapy, chemotherapy, hormonal therapy and targeted therapy. In general, the treatment may vary with the type, location and grade of the cancer as well as the patient's health and preferences. However, most of these treatments cannot produce a satisfactory effect on cancer patients due to the limitations of, for example, low-specificity, low-efficiency, and/or adverse side-effect. In view of the forgoing, there exists a need for a novel method for efficiently treating cancers so as to improve the life quality and/or life span of the cancer patients.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to an immunoconjugate that targets a protein antigen, for example, human epidermal growth factor receptor 2 (HER2). According to embodiments of the present disclosure, the immunoconjugate comprises an antibody or a fragment thereof, a functional motif, and a linker connecting the functional motif to the antibody or the fragment thereof.

The antibody or the fragment thereof comprises a heavy chain and a light chain. According to some embodiments of the present disclosure, the heavy chain comprises the amino acid sequences of LTINDYG (SEQ ID NO: 1), SIGPSGGFTS (SEQ ID NO: 2) and VIYWGFF (SEQ ID NO: 3), and the light chain comprises the amino acid sequences of NNN, YWTTY (SQ ID NO: 4) and GSNWPI (SEQ ID NO: 5). In one working example, the heavy chain comprises the amino acid sequence at least 85% identical to SEQ ID NO: 15, and the light chain comprises the amino acid sequence at least 85% identical to SEQ ID NO: 16. Preferably, the heavy chain comprises the amino acid sequence of SEQ ID NO: 15, and the light chain comprises the amino acid sequence of SEQ ID NO: 16.

According to alternative embodiments of the present disclosure, the heavy chain comprises the amino acid sequences of FTINNWG (SEQ ID NO: 6), GIWPYGGYTY (SEQ ID NO: 7) and YNHHGGV (SEQ ID NO: 8), and the light chain comprises the amino acid sequences of GSN, SWSTS (SEQ ID NO: 9) and YGGWPI (SEQ ID NO: 10). In one specific example, the heavy chain comprises the amino acid sequence at least 85% identical to SEQ ID NO: 17, and the light chain comprises the amino acid sequence at least 85% identical to SEQ ID NO: 18. Preferably, the heavy chain comprises the amino acid sequence of SEQ ID NO: 17, and the light chain comprises the amino acid sequence of SEQ ID NO: 18.

According to certain embodiments of the present disclosure, the heavy chain comprises the amino acid sequences of STIGNSG (SEQ ID NO: 11), YIGPYGGYTS (SEQ ID NO: 12) and DDYHWDG (SEQ ID NO: 13), and the light chain comprises the amino acid sequences of SGY, YSS and YYNWPV (SEQ ID NO: 14). In one working embodiment, the heavy chain comprises the amino acid sequence at least 85% identical to SEQ ID NO: 19, and the light chain comprises the amino acid sequence at least 85% identical to SEQ ID NO: 20. Preferably, the heavy chain comprises the amino acid sequence of SEQ ID NO: 19, and the light chain comprises the amino acid sequence of SEQ ID NO: 20.

The functional motif may be a therapeutic motif or a diagnostic motif. According to certain embodiments of the present disclosure, the functional motif is the therapeutic motif, which comprises a drug selected from the group consisting of an immunotoxin, immunoliposome and cytotoxic drug. In some embodiments, the drug is an immunotoxin, such as an exotoxin. For example, the exotoxin is or is derived from *Pseudomonas* Exotoxin (PE) A. In certain embodiments, the immunotoxin comprises a truncated form of PE A subunit toxin. Optionally, the therapeutic motif further comprises an endoplasmic reticulum (ER) retention peptide at the C-terminus of the PE A subunit toxin. For example, the ER retention peptide comprises the amino acid sequence of SEQ ID NO: 21 (KDEL). According to alternative embodiments, the drug is a cytotoxic drug, for example, auristatin or a derivative thereof. In one working example, the cytotoxic drug is monomethyl auristatin E (MMAE).

Alternatively, the functional motif is the diagnostic motif comprising a reporter. Non-limiting examples of the reporter include, affinity molecule, colored molecule, fluorescent molecule, luminescent molecule, phosphorescent molecule, magnetic molecule, radioisotopic molecule, peptide molecule, metal molecule, nucleic acid molecule, lipid molecule, glycosylation molecule, reactive molecule, enzyme, enzyme inhibitor, or biomolecular substrate. Optionally, the diagnostic motif may further comprise an ER retention peptide connected with the reporter.

The linker of the present immunoconjugate may be, (1) a valine-citrulline dipeptide; (2) a first polypeptide comprising the amino acid sequence of SEQ ID NO: 22; or (3) an adaptor comprising at least one AL module, wherein each AL module comprises a protein A fragment at the N-terminus, a protein L fragment at the C-terminus, and a second polypeptide connecting the protein A and protein L fragments. According to one specific example, the adaptor comprises the amino acid sequence of SEQ ID NO: 23.

Another aspect of the present disclosure pertains to a pharmaceutical composition that comprises an immunoconjugate according to any aspect and embodiment of the present disclosure, and a pharmaceutically acceptable excipient.

The third aspect of the present disclosure is directed to a method of treating a cancer in a subject. The method comprises the step of administering to the subject an effective amount of the present pharmaceutical composition.

According to embodiments of the present disclosure, the pharmaceutical composition gives rise to about 0.01 to 100 mg the present immunoconjugate per kilogram of body weight per dose; preferably, about 0.1 to 10 mg the present immunoconjugate per kilogram of body weight per dose; more preferably, about 0.5 to 5 mg the present immunoconjugate per kilogram of body weight per dose. In certain embodiments, the pharmaceutical composition is administered to the subject at least 2 times.

The fourth aspect of the present disclosure pertains to a method of making a diagnosis of a cancer in a subject in need thereof. The method comprises administering to the subject the present pharmaceutical composition.

The cancer treatable and detectable with the present method may be gastric cancer, lung cancer, bladder cancer, breast cancer, pancreatic cancer, renal cancer, colorectal cancer, cervical cancer, ovarian cancer, brain tumor, prostate cancer, hepatocellular carcinoma, melanoma, esophageal carcinoma, multiple myeloma, or head and neck squamous cell carcinoma. According to the preferred embodiments, the cancer has HER2 expressed thereon. In a specific example, the cancer is gastric or breast cancer.

The subject is a mammal, preferably, a human.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

DETAILED DESCRIPTION OF THE INVENTION

Figure 1:
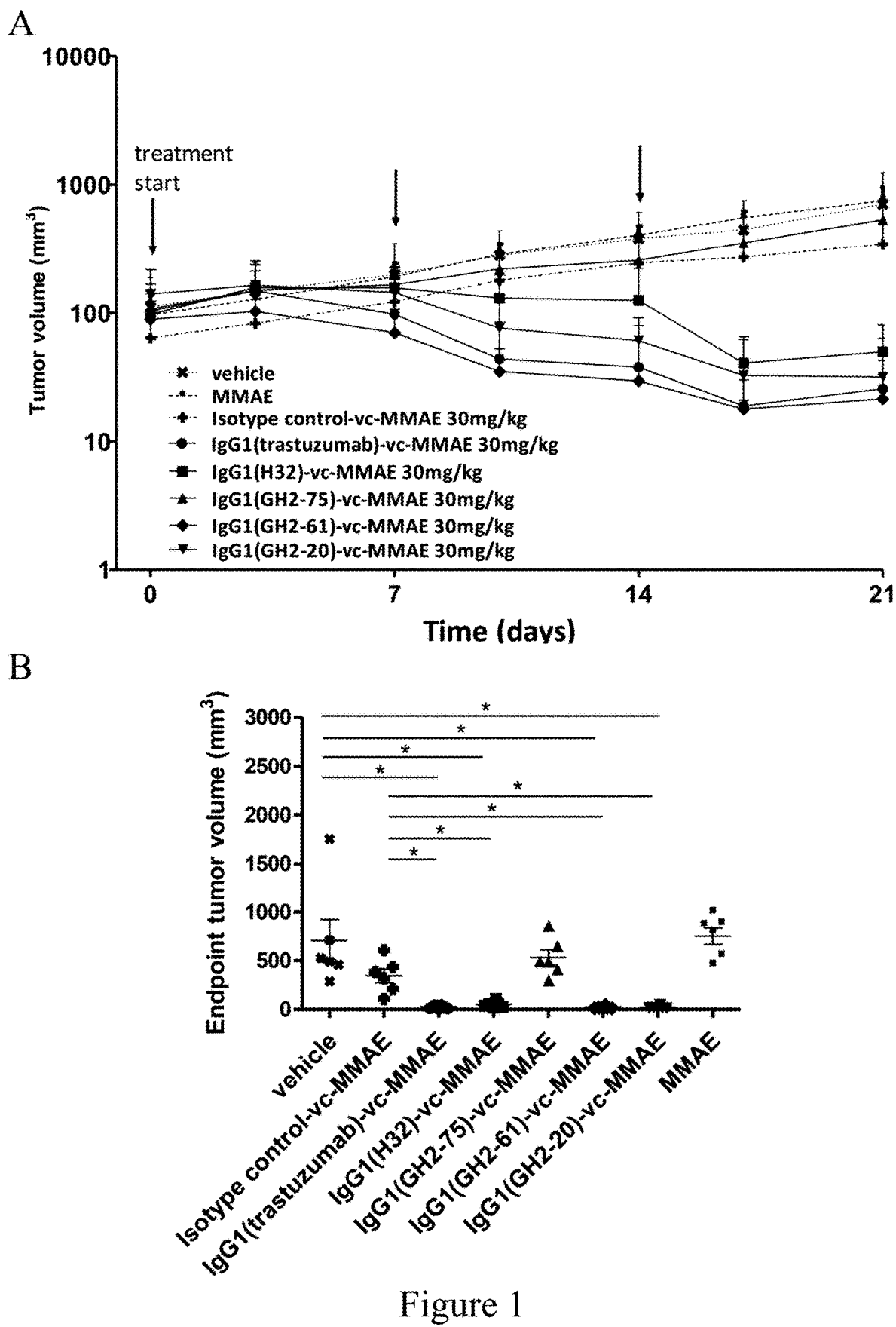
FIG. 1. Treatment of N87 xenograft mouse models with anti-HER2-ECD IgG1-vc-MMAEs. (Panel A) Time course responses of the tumor size to the IgG1-vc-MMAE treatment for xenograft mouse models bearing N87 tumors were attained from the xenograft models randomly assigned into 8 groups (n=6 per group) and treated with 30 mg/kg of respective IgG1-vc-MMAE at day 0, 7 and 14 as the arrows indicated. (Panel B) Endpoint tumor volume at day 25 for each of experimental subjects are plotted for each treatment group. (Panel C) Kaplan-Meier survival curves depict the time courses of the fraction of the animal populations surviving the IgG1-vc-MMAE treatment (defined by tumor size below 400 mm$^3$, see Materials and Methods). (Panels D-F) the description is the same as (Panels A-C) for the 10 mg/kg IgG1-vc-MMAE treatments.
Figure 1:
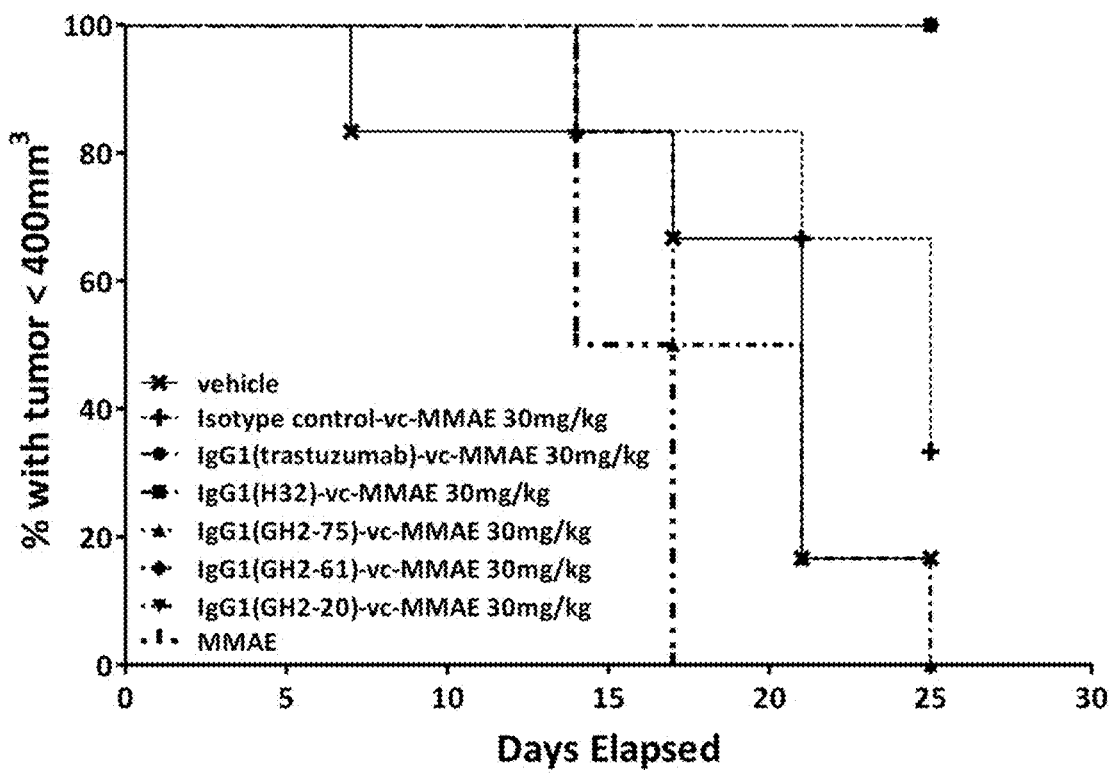
Figure 1:
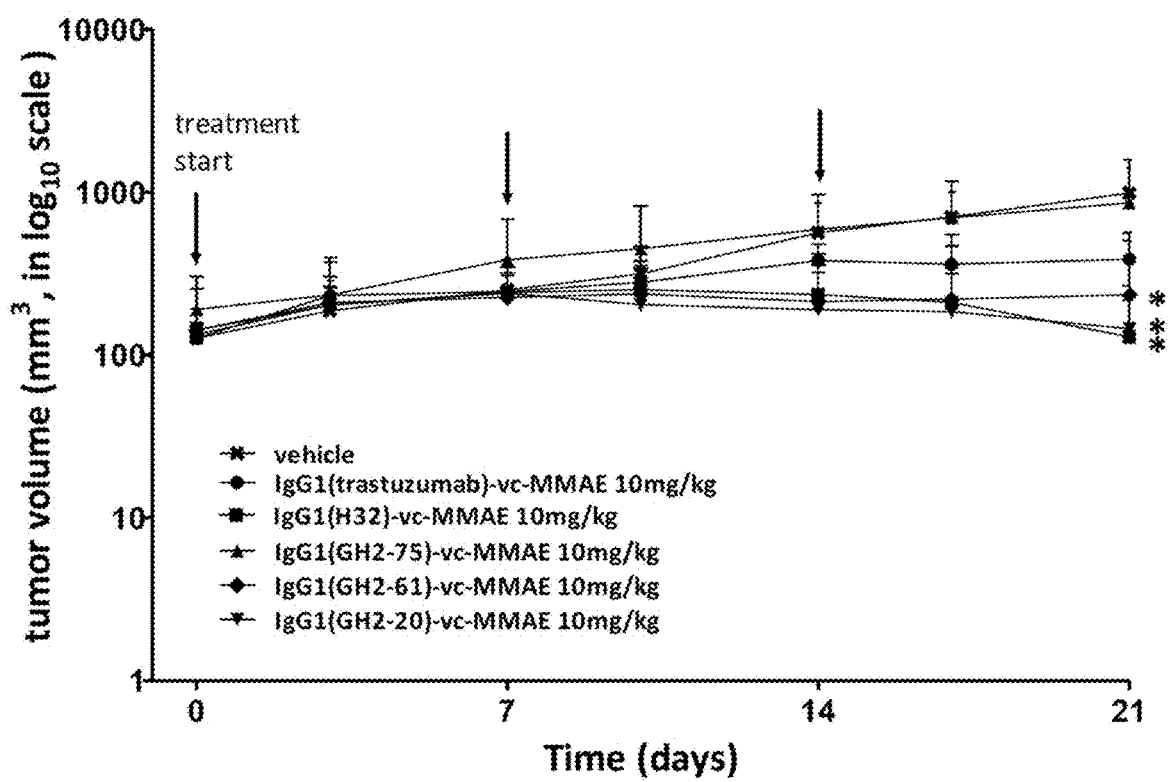
Figure 1:
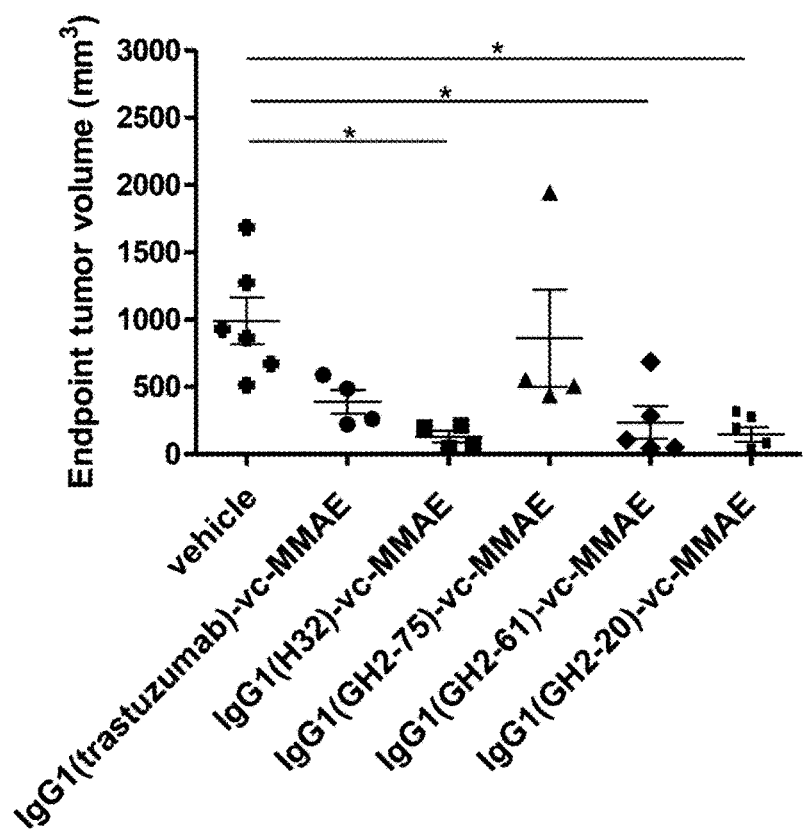
Figure 1:
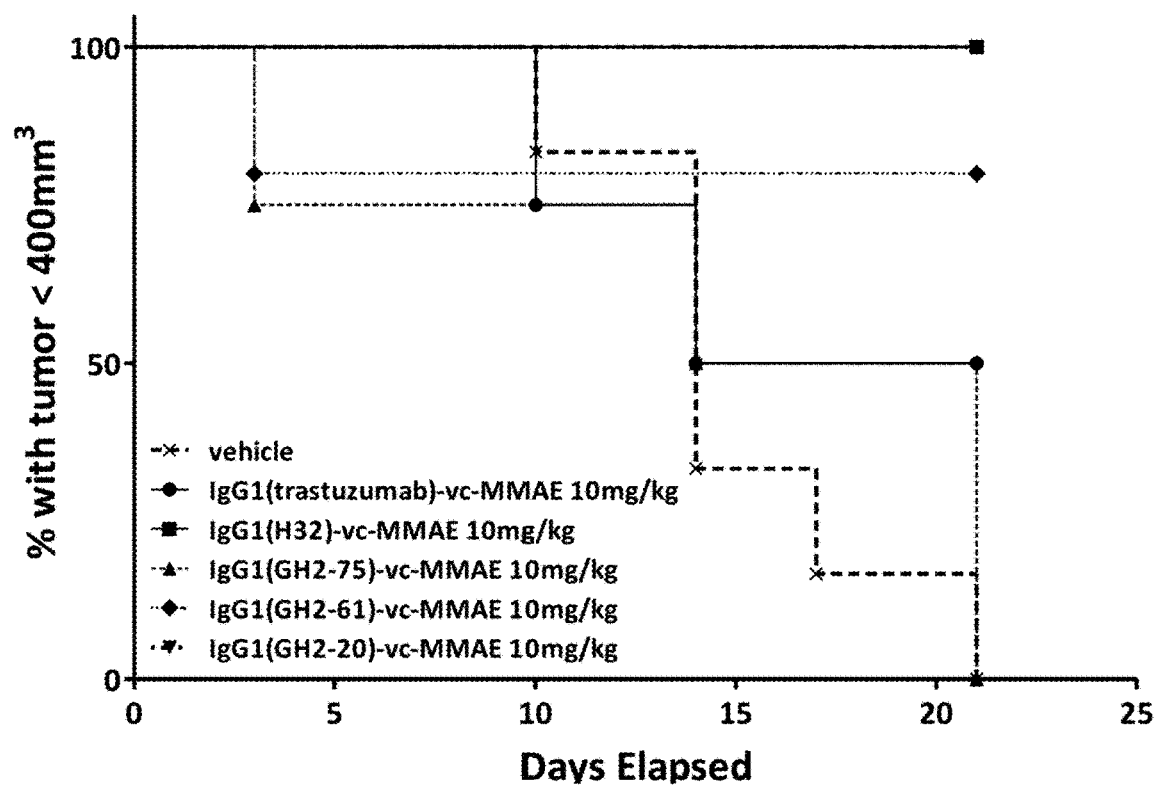

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "polypeptide" refers to a polymer of amino acids without regard to the length of the polymer; thus, "peptides," "oligopeptides," and "proteins" are included within the definition of polypeptide and used interchangeably herein. This term also does not specify or exclude chemical or post-expression modifications of the polypeptides of the invention, although chemical or post-expression modifications of these polypeptides may be included or excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. Throughout the present disclosure, the positions of any specified amino acid residues within a polypeptide are numbered starting from the N terminus of the polypeptide. When amino acids are not designated as either D- or L-amino acids, the amino acid is either an L-amino acid or could be either a D- or L-amino acid, unless the context requires a particular isomer. Further, the notation used herein for the polypeptide amino acid residues are those abbreviations commonly used in the art.

As discussed herein, minor variations in the amino acid sequences of polypeptides/peptides are contemplated as being encompassed by the presently disclosed and claimed inventive concept(s), providing that the variations in the amino acid sequence maintain at least 70% sequence identity, such as at least 70%, 71%, 72%, 73%, 75%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% sequence identity. Peptides or polypeptides of the present disclosure may be modified specifically to alter a feature of the peptide unrelated to its physiological activity. For example, certain amino acids can be changed and/or deleted without affecting the physiological activity of the peptide in this study (i.e., its ability to treat inflammation related diseases and/or conditions). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of proteins/peptides can be readily prepared by those of ordinary skill in the art. Preferred amino- and carboxy-termini of fragments or analogs occur near boundaries of functional domains. In one example, one amino acid residue (e.g., valine) of the present synthetic peptide is conservatively replaced (e.g., by leucine). In other examples, two amino acid residues of the present synthetic peptide are conservatively replaced by other suitable amino acid residues, for example, valine (V) and arginine (R) are replaced by the pair of amino acids that includes, but is not limited to, methionine (M) and lysine (K), lysine (K) and proline (P), tryptophan (W) and isoleucine (I), isoleucine (I) and proline (P), asparagine (N) and valine (V), and glutamine (G) and lysine (K).

"Percentage (%) sequence identity" is defined as the percentage of amino acid residues in a candidate sequence that are identical with the amino acid residues in the specific peptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by National Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100$$

where X is the number of amino acid residues scored as identical matches by the sequence alignment program BLAST in that program's alignment of A and B, and where Y is the total number of amino acid residues in A or B, whichever is shorter.

The term "antibody" as used herein refers to an immunoglobulin molecule which is able to specifically bind to a specific epitope on an antigen. Antibodies can be intact immunoglobulins derived from natural sources or from recombinant sources, and can be immunoreactive portions of intact immunoglobulins. Antibodies are typically tetramers of immunoglobulin molecules. An antibody can be chimeric, humanized, human and/or affinity matured.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment. The antibody fragment in the present invention may exist in a variety of forms including, for example, variable fragment (Fv), single-chain variable fragment (scFv), antigen-binding fragment (Fab) and F(ab)$_2$, as well as single chain antibodies.

The term "complementarity-determining region" (CDR) used herein refers to the hypervariable region of an antibody molecule that forms a surface complementary to the three-dimensional surface of a bound antigen. Proceeding from N-terminus to C-terminus, each of the antibody heavy and light chains comprises three CDRs (CDR-1, CDR-2 and CDR-3). An antigen combining site, therefore, includes a total of six CDRs that comprise three CDRs from the variable region of a heavy chain and three CDRs from the variable region of a light chain. The amino acid residues of CDRs are in close contact with bound antigen, wherein the closest antigen contact is usually associated with the heavy chain CDR-3.

"Binding affinity" generally refers to the strength of the sum total of noncovalent interactions between a single binding site of a molecule (e.g., an antibody or the fragment thereof) and its binding partner (e.g., an antigen). Unless indicated otherwise, as used herein, "binding affinity" refers to intrinsic binding affinity which reflects a 1:1 interaction between members of a binding pair (e.g., antibody/antibody fragment and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

The term "administered", "administering" or "administration" are used interchangeably herein to refer a mode of delivery, including, without limitation, intraveneously, intratumorally, intramuscularly, intraperitoneally, intraarterially, intracranially, or subcutaneously administering an agent (e.g., an immunoconjugate) of the present invention.

The term "treat" or "treatment" as used herein are intended to mean obtaining a desired pharmacological and/or physiologic effect. The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., a cancer) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the immunoconjugate of the present disclosure), such as molar concentration, mass concentration, volume concentration, molality, mole fraction, mass fraction and mixing ratio. Specifically, the term "therapeutically effective amount" used in connection with the immunoconjugate described herein refers to the quantity of the immunoconjugate, which is sufficient to alleviate or ameliorate the symptoms associated with cancers in the subject. Persons having ordinary skills could calculate the human equivalent dose (HED) for the medicament (such as the present immunoconjugate) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The phrase "pharmaceutically acceptable" refers to molecular entities and compositions that are "generally regarded as safe," e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or other generally recognized pharmacopeia for use in animals, and more particularly in humans.

The term "subject" refers to a mammal including the human species that is treatable with the immunoconjugate and/or methods of the present invention. The term "subject" is intended to refer to both the male and female gender unless one gender is specifically indicated.

II. Description of the Invention

The present disclosure aims at providing a method for efficiently treating cancers by use of a novel immunoconjugate. Structurally, the present immunoconjugate comprises an antibody (e.g., an IgG) or a fragment thereof (e.g., an scFv), a functional motif, and a linker for connecting the antibody/antibody fragment and the functional motif. The antibody/antibody fragment exhibits binding affinity and/or specificity to a tumor-associated antigen (TAA) expressed/overexpressed on tumor cells. Such antibody/antibody fragment may serve as a targeting module for delivering the agent (e.g., a drug or a reporter) connected therewith to the tumor cells in a subject.

According to some embodiments, the cancer has HER2 expressed thereon, for example, a gastric cancer or a breast cancer.

The present antibody/antibody fragment selected from the method described in co-pending U.S. application Ser. No. 15/619,835 comprises a heavy chain and a light chain. In certain embodiments of the present disclosure, the complementarity-determining region-1 (CDR-1), CDR-2 and CDR-3 of the heavy chain comprises the amino acid sequences of LTINDYG (SEQ ID NO: 1), SIGPSGGFTS (SEQ ID NO: 2) and VIYWGFF (SEQ ID NO: 3), and the CDR-1, CDR-2 and CDR-3 of the light chain comprises the amino acid sequences of NNN, YWTTY (SEQ ID NO: 4) and GSNWPI (SEQ ID NO: 5). According to some working examples of the present disclosure, the heavy chain and the light chain of the antibody/antibody fragment respectively comprise the amino acid sequences at least 85% (i.e., 85, 86, 87, 88, 89, 90, 91, 92, 93, 94, 95, 96, 97, 98, 99 or 100%) identical to SEQ ID NOs: 15 and 16. In one specific example, the heavy chain and the light chain of an antibody designated as GH2-20 respectively comprise the amino acid sequences 100% identical to SEQ ID NOs: 15 and 16.

Alternatively, the CDR-1, CDR-2 and CDR-3 of the heavy chain comprises the amino acid sequences of FTINNWG (SEQ ID NO: 6), GIWPYGGYTY (SEQ ID NO: 7) and YNHHGGV (SEQ ID NO: 8), and the CDR-1, CDR-2 and CDR-3 of the light chain comprises the amino acid sequences of GSN, SWSTS (SEQ ID NO: 9) and YGGWPI (SEQ ID NO: 10). In certain embodiments of the present disclosure, the heavy chain and the light chain of the antibody/antibody fragment respectively comprise the amino acid sequences at least 85% identical to SEQ ID NOs: 17 and 18. In one working example, the heavy chain and the light chain of an antibody designated as GH2-61 respectively comprise the amino acid sequences 100% identical to SEQ ID NOs: 17 and 18.

According to certain embodiments, the CDR-1, CDR-2 and CDR-3 of the heavy chain comprises the amino acid sequences of STIGNSG (SEQ ID NO: 11), YIGPYGGYTS (SEQ ID NO: 12) and DDYHWDG (SEQ ID NO: 13), and the CDR-1, CDR-2 and CDR-3 of the light chain comprises the amino acid sequences of SGY, YSS and YYNWPV (SEQ ID NO: 14). In some specific examples, the heavy chain and the light chain of the antibody/antibody fragment respectively comprise the amino acid sequences at least 85% identical to SEQ ID NOs: 19 and 20. In the preferred example, the heavy chain and the light chain of an antibody designated as GH2-75 respectively comprise the amino acid sequences 100% identical to SEQ ID NOs: 19 and 20.

As would be appreciated, the amino acid sequences of the heavy chain and light chain of the antibody may vary with the TAA targeted. For example, one skilled artisan in the art may select antibodies with suitable heavy chains and light chains recognizing alpha-fetoprotein (AFP) thereby delivering the present immunoconjugate to hepatocellular carcinoma. Depending on the TAA targeted, the cancers treatable with the present immunoconjugate include, but are not limited to, gastric cancer, lung cancer, bladder cancer, breast cancer, pancreatic cancer, renal cancer, colorectal cancer, cervical cancer, ovarian cancer, brain tumor, prostate cancer, hepatocellular carcinoma, melanoma, esophageal carcinoma, multiple myeloma, and head and neck squamous cell carcinoma.

Depending on desired purposes, the functional motif may be a therapeutic motif or a diagnosis motif. According to certain embodiments of the present disclosure, the functional motif is the therapeutic motif comprising a drug, and optionally, an ER retention peptide (e.g., KDEL, SEQ ID NO: 21) connected with the drug. The drug may be an immunotoxin, immunoliposome or cytotoxic drug. Non-limiting examples of the immunotoxin include, diphtheria A subunit, nonbinding fragments of diphtheria toxin, exotoxin A subunit, ricin A subunit, abrin A subunit, modeccin A subunit, alpha-sarcin, *Aleurites fordii* proteins, dianthin proteins, *Phytolacca americana* proteins (PAPI, PAPII, and PAP-S), *Momordica charantia* inhibitor, curcin, crotin, *Saponaria officinalis* inhibitor, gelonin, mitogellin, restrictocin, phenomycin, and enomycin. According to some preferred embodiments, the immunotoxin is exotoxin; more preferably, the immunotoxin is or is derived from *Pseudomonas* Exotoxin (PE) A. In one working example of the present disclosure, the immunotoxin is a truncated form of PE A subunit toxin.

Examples of the cytotoxic drug include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel, docosahexaenoic acid bound-paclitaxel (DHA-paclitaxel, Taxoprexin), polyglutamate bound-paclitaxel (PG-paclitaxel, paclitaxel poliglumex), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), Ca' ATPase inhibitors (e.g. thapsigargin), imatinib, thalidomide, lenalidomide, tyrosine kinase inhibitors (e.g., axitinib, bosutinib, cediranib, dasatinib, erlotinib, gefitinib, imatinib, lapatinib, lestaurtinib, neratinib, nilotinib, semaxanib, sunitinib, toceranib, vandetanib, vatalanib, trastuzumab, bevacizumab, rituximab, cetuximab, panitumumab, ranibizumab, nilotinib, sorafenib, everolimus, alemtuzumab, gemtuzumab ozogamicin, temsirolimus, dovitinib lactate, and tivozanib), proteasome inhibitors (e.g., bortezomib), mTOR inhibitors (e.g., rapamycin, temsirolimus, everolimus, and ridaforolimus), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. According to one specific example of the present disclosure, the cytotoxic drug is auristatin or a derivative thereof (e.g., MMAE or MMAF).

The immunoliposome comprises at least one active agent (e.g., immunotoxin and/or cytotoxic drug) encapsulated in the liposome structure. The liposome may be a large unilamellar vesicle (LUV), a multilamellar vesicle (MLV) or a small unilamellar vesicle (SUV), depending on desired purposes.

Alternatively, the functional motif may be the diagnostic motif comprising a reporter and optionally a ER retention peptide connected therewith. Exemplary reporters include, but are not limited to, affinity molecule, colored molecule, fluorescent molecule, luminescent molecule, phosphorescent molecule, magnetic molecule, radioisotopic molecule, peptide molecule, metal molecule, nucleic acid molecule, lipid molecule, glycosylation molecule, reactive molecule, enzyme, enzyme inhibitor, or biomolecular substrate.

The linker may be a valine-citrulline (vc) dipeptide, a polypeptide, a DNA, a RNA, an aliphatic chain, or an adaptor. According to some embodiments of the present disclosure, the linker is a valine-citrulline dipeptide; in these embodiments, the immunoconjugate is present in the form of IgG-vc-drug, in which the drug (e.g., MMAE) is connected to the cysteine residues of the IgG antibody via the valine-citrulline dipeptide. According to certain embodiments of the present disclosure, the linker is a polypeptide having the sequence of SEQ ID NO: 22; the thus-produced immunoconjugate comprises an scFv, a polypeptide and a therapeutic motif PE38DKEL (SEQ ID NO: 31), in sequence, from N-terminus to C-terminus, in which the therapeutic motif PE38DKEL comprises a truncated form of PE A subunit toxin (i.e., PE38; SEQ ID NO: 32) and a ER retention peptide (i.e., KDEL; SEQ ID NO: 21). According to alternative embodiments of the present disclosure, the linker is an adaptor comprising one or more AL module, in which each AL module comprises a protein A fragment at the N-terminus, a protein L fragment at the C-terminus, and a polypeptide connecting the protein A and protein L fragments. In one working examples, the IgG antibody is connected to the therapeutic motif (e.g., PE38KDEL) via one AL module, which comprises the amino acid sequence of SEQ ID NO: 23.

The second aspect of the present disclosure is directed to a pharmaceutical composition comprising the immunoconjugate in accordance with any embodiment of the present disclosure, and a pharmaceutically acceptable excipient.

Generally, the present immunoconjugate is present in the pharmaceutical composition at a level of about 0.01% to 99.9% by weight, based on the total weight of the pharmaceutical composition. In some embodiments, the present immunoconjugate is present at a level of at least 0.1% by weight, based on the total weight of the pharmaceutical composition. In certain embodiments, the present immunoconjugate is present at a level of at least 5% by weight, based on the total weight of the pharmaceutical composition. In still other embodiments, the present immunoconjugate is present at a level of at least 10% by weight, based on the total weight of the pharmaceutical composition. In still yet other embodiments, the present immunoconjugate is present at a level of at least 25% by weight, based on the total weight of the pharmaceutical composition.

The pharmaceutical composition may comprise different types of excipients or carriers depending on the intended routes of administration. The present pharmaceutical composition may be administered intraveneously, intradermally, intraarterially, intraperitoneally, intralesionally, intracranially, intranasally, intrapleurally, intratracheally, intrarectally, topically, intramuscularly, subcutaneously, intravesicularlly, intrapericardially, intraocularally, intratumorally, orally, topically, locally, injection, inhalation, infusion, localized perfusion, in any suitable forms such as powders, creams, liquids, aerosols and etc.

The present pharmaceutical composition may be formulated into solid, semi-solid, or liquid forms, such as tablets, capsules, powders, granules, ointments, solutions, suppositories, and injections. As such, administration of the present immunoconjugate can be achieved in various ways, including oral, buccal, rectal, parental, intraperitoneal, and etc. administration. In pharmaceutical dosage forms, the present immunoconjugate may be administered alone or in combination with other known pharmaceutically active agent to treat diseases and conditions caused by/associated with cancers. One of skilled person in the art is familiar with the various dosage forms that are suitable for use in each route. It is to be noted that the most suitable route in any given case would depend on the nature or severity of the disease or condition being treated.

The third aspect of the present disclosure pertains to a method of treating a cancer in a subject. The method comprises administering to the subject an effective amount of the present immunoconjugate or pharmaceutical composition in accordance with any aspect and embodiment of the present disclosure.

In one embodiment, the subject is a mouse. To elicit a therapeutic effect in mice, about 0.1 to 1200 mg of present immunoconjugate per Kg body weight per dose is administered (i.e., the present immunoconjugate is administered to the subject in the amount of about 0.1 to 1200 mg per Kg body weight per dose; alternatively, in the case when the pharmaceutical composition is administered to the subject, it gives rise to about 0.12 to 1200 mg of the present immunoconjugate per Kg body weight per dose); for example, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1100 or 1200 mg per Kg body weight per dose. Preferably, about 1 to 120 mg of the present immunoconjugate per Kg body weight per dose is administered. According to one working example, 6 to 60 mg of the present immunoconjugate per Kg body weight per dose is sufficient to elicit a tumor-specific cytotoxic response (e.g., inhibiting tumor growth) in the subject.

A skilled artisan could calculate the human equivalent dose (HED) of the present immunoconjugate, based on the doses determined from animal models. Accordingly, the effective amount of the present immunoconjugate suitable for use in a human subject may be in the range of 0.01 to 100 mg per Kg body weight per dose for human, for example, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg per Kg body weight per dose. Preferably, the effective HED is about 0.1 to 10 mg per Kg body weight per dose. In one preferred example, the effective HED is about 0.5 to 5 mg per Kg per dose.

The effective amount of the present immunoconjugate or the pharmaceutical composition may vary with many factors, such as the physical condition of the patient (e.g., the patient's body mass, age, or gender), the severity of the condition, the type of mammal or animal being treated, the duration of the treatment, and the nature of concurrent therapy (if any), and the specific route of administration and like factors within the knowledge and expertise of the health practitioner.

For repeated administrations over several days or longer, depending on the condition, the treatment is sustained until a desired suppression of symptoms occurs or until sufficient therapeutic levels are achieved to alleviate the cancer, or a symptom thereof. According to some embodiments of the present disclosure, the present immunoconjugate or pharmaceutical composition is administered to the subject at least 2 times, for example, 2, 3, 4, 5 or more times. The dosing frequency may be once every day, every 2 days, every 3 days, every 4 days, every 5 days, every 6 days, every week, every 2 weeks, every 3 weeks, every month, every 2 months, every 3 month, or longer. In one working example, the present immunoconjugate is administered every weeks for 3 consecutive weeks. In an alternative example, the present immunoconjugate is administered 3 times in one week.

The immunoconjugate or pharmaceutical composition may be administered intraveneously, intradermally, intraarterially, intraperitoneally, intralesionally, intracranially, intranasally, intrapleurally, intratracheally, intrarectally, topically, intramuscularly, subcutaneously, intravesicularlly, intrapericardially, intraocularally, intratumorally, orally, topically. According to one embodiment, the immunoconjugate/pharmaceutical composition is intraveneously administered to the subject. According to another embodiment, the immunoconjugate/pharmaceutical composition is intrapericardially administered to the subject.

Basically, the subject is a mammal, for example, a human, a mouse, a rat, a hamster, a guinea pig, a rabbit, a dog, a cat, a cow, a goat, a sheep, a monkey, and a horse. Preferably, the subject is a human.

As would be appreciated, the present method can be applied to the subject, alone or in combination with additional therapies that have some beneficial effects on the treatment of cancers. Depending on the intended/therapeutic purposes, the present method can be applied to the subject before, during, or after the administration of the additional therapies.

Another aspect of the present disclosure is directed to a method of making a diagnosis of a cancer in a subject in need thereof. The method comprises administering to the subject the present immunoconjugate or pharmaceutical composition in accordance with any aspect and embodiment of the present disclosure.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Cell Culture and Tumor Xenograft Studies

Human gastric carcinoma cell line NCI-N87 was acquired from American Type Culture Collection (ATCC). The cells were grown in RPMI 1640 medium containing 10% fetal bovine serum and Pen/Strep (10,000 U penicillin, 10 mg streptomycin) at 37° C. in a humidified incubator containing 5% $CO_2$. All mouse experiments were conducted according to relevant guidelines and experimental protocols approved by the Institutional Animal Care and Utilization Committee (IACUC) of Academia *Sinica*. The N87 tumor-bearing mouse model was established by subcutaneously inoculating $1 \times 10^6$ cells into the right flank of 6-8 week old male NOD.CB17-Prkdc$^{scid}$d/NcrCrlBltw NOD/SCID mice. When the tumors reached suitable tumor size of 80-100 $mm^3$, the mice were randomly assigned into control and treatment groups and dosing was started. N87 tumor-bearing mice were treated once a week for a total of three doses with antibody-based anti-HER2 therapeutics through intravenous injection unless otherwise stated. The measurements of tumor size and weight change in mice were recorded twice a week. Tumor volume was calculated using the ellipsoid formula: length×width×height×0.523. Survival probability over time was evaluated by the Kaplan-Meier method; mice with tumor of the size above 400 $mm^3$ were considered as treatment failures and were removed from the surviving population in calculating the Kaplan-Meier curves.

IgG1-vc-MMAE Preparation

The IgG1s were conjugated with vc-MMAE through the cysteine residues on the TCEP-reduced IgG1s. Briefly, antibody was partially reduced for 1 hour at room temperature with tris(2-carboxyethyl)phosphine (TECP). The concentration of the reductant was adjusted to achieve equal DAR in the product ADCs: IgG1(trastuzumab), IgG1(H32), and isotype control antibodies were reduced with 28 μM TCEP (2 equivalent of reductant-to-IgG1 molar ratio), IgG1(GH2-75), IgG1(GH2-61), and IgG1(GH2-20) antibodies were reduced with 42 μM TCEP (3 equivalent of reductant-to-IgG1 molar ratio). The reduced antibodies were conjugated with drug by adding 5.25 equivalents of maleimide-vc-MMAE (10 mM DMSO solved stock). The conjugation reaction was kept at room temperature for 1 hour. The N-acetylcystein was used to quench the reaction at room temperature for 30 minutes. The quenched reaction mixture was desalted by gel filtration with a 5 mL desalting column; the buffer was changed into PBS and the ADC product was concentrated by centrifugal ultrafiltration. The ADC solutions were filtered through a 0.2 μm filter and stored at 4° C. The ADC products were analyzed by sodium dodecyl sulfate-polyacrylamide electrophoresis (SD S-PAGE) and hydrophobic interaction chromatography (HIC).

scFv-PE38KDEL Preparation

The amino acid sequence of PE38KDEL domain has been documented; the peptide linker (ASAAGGSGT; SEQ ID NO: 22) was inserted between scFv (with VL-linker-VH orientation) and PE38KDEL domain. The codon optimized nucleotide sequences were chemically synthesized. The construction, expression and purification of scFv-PE38KDEL were similar to previously described protocols. In brief, the scFv-PE38KDEL coding region was sub-cloned into pET-32a expression vector with a thioredoxin fusion N-terminal to the scFv-PE38KDEL; the fusion protein contains a hexa-HIS tag followed by a TEV protease cutting site between the thioredoxin and the scFv-PE38KDEL. *E. coli* transformed with scFv-PE38KDEL-pET32a expression vector were grown in 2× YT medium (Tryptone 16 g/L, Yeast extract 10 g/L, NaCl 5 g/L) with ampicillin (200 μg/L), tetracycline (12.5 μg/L) and chloramphenicol (37.5 μg/L) at 37° C. until OD 600 reached 1.0, and then were shifted to 16° C. for additional 1 hour incubation to reach temperature equilibrium between incubator and culture media. The protein expression was induced with final 0.2 mM IPTG overnight. The cell pellets were processed in lysis buffer (Tris-HCl, 20 mM, pH 8.0, 300 mM NaCl) with MICROFLUIDIZER®. The recombinant thioredoxin fusion scFv-PE38KDEL immunotoxin was purified by nickel chelation chromatography with $Ni^{2+}$ charged IMAC prepacked column. The fractions containing scFv-PE38KDEL immunotoxin were collected and digested by TEV protease (OD280 ratio 50:1) at 30° C. for at least 5 hours, and then dialyzed against PBS buffer overnight. The hexa-HIS tag containing thioredoxin and TEV protease were removed by Ni' charged IMAC prepacked column. The tag-free scFv-PE38KDEL immunotoxin in the flow-through was collected and further purified with a size-exclusion column in PBS to around 95% purity (data not shown).

Cellular Uptake and Internalization of HER2-Targeting IgG1s

For internalization assays, the procedure was based on the previous literature with some minor modifications. In brief, N87 cells ($1 \times 10^6$) were seeded in a 6-well plate and cultured in 3 mL of culture medium. After 24 hour incubation, the culture medium was replaced by the serum-free medium containing radiolabeled anti-HER2 antibodies (3 mL, 0.074 MBq/mL). At designated time points (4, 12, 24, and 48 hours post-incubation), the radioactive medium was aspirated, and the cells were washed with PBS (0.5 mL) to remove unbound radiolabeled antibodies. The medium and washing PBS were collected into a counting vial. 0.5% trypsin (0.5 mL) was added to detach the cells from the plate. Serum-containing culture medium (1.5 mL) was added to re-suspend the cells for avoiding possible damage from trypsin treatment. The number of cells in the cell suspension was counted for normalizing the cellular uptake of the radiolabeled antibody. The cellular uptake was expressed as the percentage of treated dose accumulated in one million cells. After radioactivity measurement, the collected cells from cellular uptake assays were treated with 1 mL solution of 200 nM sodium acetate and 500 nM sodium chloride (pH=2.5) at 4° C. for 5 minutes and then centrifuged at 8,000 g for 10 minutes. The cells were washed twice with PBS. The supernatant of cell suspension and washing buffer were collected into a vial, and the cell pellets were added to another counting vial for radioactivity measurement. The percentage of cellular IgG1 uptake per one million cells was calculated by the equation:

% cellular uptake=100×cell radioactivity count (after acid wash)/total radioactivity count where, total radioactivity count=cell count (before acid wash)+medium count IgG1 Preparation Antibody IgG1s were produced by recombinant IgG vector transfection to 293 cells. 293 cells were kept in culture medium with vent-cap baffled flask for better activity. Transfection was performed using EXPIFECTAMINE™ 293 Transfection Kit according to the manufacturer's instructions. After 3 days of incubation, the antibodies in supernatant was purified using Protein A affinity chromatography. The purity of the antibodies was analyzed by sodium dodecyl sulfate-polyacrylamide electrophoresis (SDS-PAGE), and the concentration was determined by spectrophotometry.

Hydrophobic Interaction Chromatography (HIC) Analysis

The ADC samples were analyzed using HIC: AKTA Purifier 10 FPLC System; TSKgel Butyl-NPR column; solvent A, 50 mM phosphate and 1.5 M amino sulfate pH 7.0; solvent B, 50 mM phosphate pH 7.0. 25 µg ADC sample prepared in a 50 µL solvent B with 300 mM amino sulfate. The gradient was 20-80% A/20-80% B to 100% B at 1 mL/min flow rate; the UV detection wavelength was set at 280 nm. To achieve a good resolution of chromatogram, the following elution conditions were used: for IgG1(trastuzumab), IgG1(H32) and their corresponding ADCs, 20% A/80% B to 100% B gradient of mobile phases was used; for IgG1(GH2-61) and its ADC, 50% A/50% B to 100% B gradient of mobile phases was used; for IgG1(GH2-75), IgG1(GH2-20) and their ADCs, 80% A/20% B to 100% B gradient of mobile phases was used. The identification for peaks corresponding to ADCs with two, four, and six drugs per antibody was accomplished, and the drug/mAb ratio (DAR) was determined by peak area integration.

Measurements of $EC_{50}$ with ELISA for HER2 Binding

For determining the $EC_{50}$ of purified HER2 antibodies, DyLight 680- or DTPA-conjugated HER2 antibodies and scFv-PE38KDEL immunotoxins to HER2-ECD, the ELISA assays were carried out as described previously with minor modifications. Briefly, the HER2-ECD antigen (0.3 µg per well) was coated in PBS buffer (pH 7.4) on 96-well plates overnight at 4° C., and blocked with 5% milk in PBST [0.1% (v/v) Tween 20] for 1 hour. In the meantime, antibodies in PBST with 5% milk were prepared at 11 concentrations by two-fold serial dilution, and then added 100 µL diluted samples to the plate. After 1 hour of binding and washing three times with PBST, 100 µL 1:3000 anti-*Pseudomonas* Exotoxin A antibody (Rabbit serum) was added to each well for 1 hour incubation. After washing three times with PBST, 100 µL 1:10,000 anti-human IgG horseradish peroxidase antibody or 1:5000 horseradish peroxidase/anti-rabbit IgG antibody conjugate was added for 1 hour incubation. After washing three times with PBST and twice with PBS buffer, the plate was developed for 3 minutes with 3,3',5,5'-tetramethyl-benzidine peroxidase substrate (TMB substrate), quenched with 1.0 M HCl and read spectrophotometrically at 450 nm. The $EC_{50}$ (nM) was then calculated.

Antibody-Antigen Interaction Affinity and Kinetics Measurements by Surface Plasmon Resonance Binding affinities and kinetics between IgGs and HER2-ECD were analyzed by surface plasmon resonance in capture mode with BIACORE™ T200 instrument. Anti-human Fc antibody was immobilized on a sensor chip via amine coupling protocol. Each flow cell was verified with capturing 100-200 response units of IgGs or ADCs, prepared in HBS-EP⁺ buffer at the concentration of 20 ng/mL, injected at 10 µL flow rate for 20 seconds. Five different concentrations of HER2-ECD solutions (4, 8, 16, 32, 64 nM) were assayed for the IgGs or ADCs binding kinetics. In the multiple kinetics assay, solution of HER2-ECD was injected with a flow rate of 30 µL/min for 120-180 seconds to determine association rate ($k_{on}$), and flowed with HBS-EP⁺ buffer at 30 µL/min for 280-300 seconds to determine dissociation rate ($k_{off}$). After a binding cycle, all the capture surfaces were regenerated by injection with 3M $MgCl_2$ for 30 seconds at the flow rate of 30 µL/min. Finally, the binding affinity and kinetics constants were deduced from the curve fitting on sensorgrams by surface binding/kinetics fitting in 1:1 binding model, using the BIA-evaluation software.

Flow Cytometry

N87 cells ($3\times10^5$) were re-suspended in 96-well plates and stained with 15 µg/mL corresponding anti-HER2 IgG1 and IgG1-vc-MMAE for 30 minutes at 4° C. After staining, cells were washed twice with PBS and then further incubated with Alexa Fluor 633-labeled antibody against human IgG for 30 minutes at 4° C. The fluorescence intensity was analyzed using a flow cytometer.

Pharmacokinetic Measurement

Each of the 6-week-old male NOD/SCID mice was injected via tail vein with 100 µg/kg antibody/ADC (four mice per antibody/ADC, n=4). To assess circulating level of total and conjugated antibody, blood samples were collected via orbital sinus from mice at 5, 24, 49, 78, 144, 216 and 311 hours post-injection. The clotted blood was centrifuged at 3000 g for 20 minutes at 4° C. to separate the serum and stored at −70° C. before analyses. Total IgG1 concentration in the serum samples was measured as follows: the HER2-ECD antigen (0.3 µg per well) was coated in PBS buffer (pH 7.4) on 96-well plates overnight at 4° C., and blocked with 5% milk in PBST [0.1% (v/v) Tween 20] for 1 hour. The plates were washed with PBST, and standard or diluted blood samples were added to the plate. After 1 hour of binding and washing three times with PBST, 100 µL 1:10,000 anti-human IgG horse-radish peroxidase antibody was added to each well for 1 hour incubation. After washing three times with PBST and twice with PBS buffer, the plate was developed for 3 minutes with 3,3',5,5'-tetramethyl-benzidine peroxidase substrate (TMB substrate), quenched with 1.0 M HCl and read spectrophotometrically at 450 nm. The concentration of total IgG1 in the samples was extrapolated from a four-variable fit of the standard curve. For measurements of ADC concentrations, wells were coated with HER2-ECD antigen (0.3 µg per well) and serum samples were added as described above. After 1 hour incubation, plates were washed and 100 µL 1:1000 mouse anti-MMAE antibody was added for another 1 hour incubation. After washing three times with PBST, 100 µL 1:2000 anti-mouse IgG horseradish peroxidase antibody was added for 1 hour incubation. Color development were performed as described above.

Serum Biochemical Analysis 10-week-old male NOD/SCID mice were intraperitoneally injected with 0.75 mg/kg anti-HER2 IgG1-AL1-PE38KDELs twice a week or 30 mg/kg anti-HER2 IgG1-vc-MMAEs once a week for a total of three doses. The blood samples were collected as described above and assayed for alanine transaminase (ALT), alkaline phosphatase (ALP), creatinine (CRE) and blood urea nitrogen (BUN) using FUJI DRI-CHEM 4000i according to manufacturer's instructions.

Cytotoxicity ($IC_{50}$) Measurements for ADCs

N87 cells ($1\times10^4$) were seeded in 96-well plates for the $IC_{50}$ measurements of cell viability. For IgG1-AL1-PE38KDEL, IgGs were pre-incubated with AL1-PE38KDEL at a molar ratio of 1:2 for IgG:AL fragment for 1 hour at room temperature. This procedure allows the formation of non-covalently linked immunotoxins. IgG1-AL1-PE38KDEL mixtures, scFv-PE38KDELs or IgG1-vc-MMAEs were added to culture medium without serum. After incubation at 37° C. for 16 hours, the medium was replaced by fresh normal medium with serum and the cytotoxicity was assessed using the WST-1 reagent after 72 hours of incubation at 37° C. Values were normalized by corresponding PBS-treated control cells as 100% viability and $IC_{50}$ values were calculated.

Confocal Microscopy

N87 cells were incubated with 5 µg/mL antibody at 4° C. for 30 minutes or at 37° C. for 18 hours. After incubation, cells were washed with PBS, fixed and permeabilized by a fixation/permeabilization solution in accordance with a standard protocol. Cells were stained with Alexa Fluor 633-labeled antibody against human IgG to detect receptor-antibody complex (red), and rabbit anti-human LAMP2 followed by Alexa Fluor 488-labeled anti-rabbit IgG to detect lysosomes (green). After staining, cells were coverslipped with VECTASHIELD® mounting medium containing DAPI and analyzed under a confocal microscope.

Western Blot Analysis

Cells were treated with 10 µg/mL of IgG1(trastuzumab)-vc-MMAE, IgG1(H32)-vc-MMAE, IgG1(GH2-75)-vc-MMAE, IgG1(GH2-61)-vc-MMAE or IgG1(GH2-20)-vc-MMAE for 18 hours, and then stimulated with 100 ng/mL heregulin-1β for 10 minutes. Cell extracts were prepared by scraping in RIPA lysis buffer containing protease inhibitor cocktail and phosphatase inhibitor cocktail. The lysate was spun down at 14,000 r.p.m for 20 minutes at 4° C., and the protein content was measured before loading. Immunoblot analysis was performed after NuPAGE 4 to 12% gradient gels under reducing conditions in accordance with the manufacturer's instructions. After overnight incubation with 1:500 dilution of anti-phospho-HER2, or 1:1,000 dilution of anti-HER2, anti-Akt, anti-phospho-Akt, anti-Erk1/2, anti-phospho-Erk1/2 antibodies followed by a 5,000 dilution of horseradish peroxidase-conjugated anti-rabbit secondary antibody. The intensity of immunoreactive bands were detected. Image capture was performed on an IMAGEQUAN LAS 4000.

Maleimide-DyLight 680 Conjugation and In Vivo Optical Imaging 15-fold molar excess of tris(2-carboxyethyl)phosphine (TECP) were used to reduce IgG1(trastuzumab), IgG1(H32), IgG1(GH2-75), IgG1(GH2-61) and IgG1(GH2-20) for 2 hours at room temperature. A 10-fold molar excess of DyLight 680 was then added and the reaction mixture was kept at room temperature to react for 2 hours. Excess dye was removed, and conjugation efficiency was determined to calculate the molar ratio of DyLight 680 to protein. Mice were intravenously injected with 0.5 nmol DyLight680-anti-HER2 antibodies or DyLight680-isotype negative control IgG, and were NIRF imaged using a small-animal imaging system with excitation and emission wavelengths of 682 and 715 nm at 24 hours. Fluorescence emission was normalized to photons per second per centimeter squared per steradian (p/s/cm2/sr).

Ex Vivo NIRF Imaging

N87 tumor bearing mice were intravenously injected with 0.5 nmol of DyLight 680-anti-HER2 IgG1 antibodies. After 24 hours post-injection, mice were euthanized, the organs and blood were collected and were NIRF imaged using a small-animal imaging system with excitation and emission wavelengths of 675 and 720 nm. Fluorescence emission was normalized to photons per second per centimeter squared per steradian (p/s/cm2/sr).

MicroSPECT/CT Imaging

The microSPECT/CT imaging studies were performed at Chang Gung Memorial Hospital (Taiwan). The mice were randomly divided into five groups intravenously administered with 18.5 MBq (0.1 mg/mouse) of $^{111}$In-IgG1(trastuzumab), $^{111}$In-IgG1(H32), $^{111}$In-IgG1(GH2-75), $^{111}$In-IgG1(GH2-61), and $^{111}$In-IgG1(GH2-20), respectively. Static imaging was carried out for around 30 minutes at 24 and 48 hours after injection. Regions of interest (ROIs) were drawn over the tumor (T) and muscle (M), and the average intensity of the pixels within ROIs was corrected by subtracting the background radioactivity, which is measured in the remote areas away from the body. The specific tumor accumulation was expressed as the tumor-to-muscle ratio (T/M) for parallel comparison.

Pooled CRISPR-Cas9 Genome-Wide Knock-Out N87 Cells Treated with IgG1-AL1-PE38KDELs Immunotoxins-Preparation of GeCKO v2 Lentiviral Library The GeCKO v2 lentiviral library was prepared by the national RNAi core facility in Taiwan. In brief, HEK293T cells (ATCC) were seeded the day before transfection in 25 mL DMEM supplemented with 10% FBS. Cells were grown to 80% confluence and transfected. For each 10-cm cell culture dish, prepare a DNA mixture containing 12.5 µg of GeCKO v2 lentiGuide plasmid library, 11.25 µg of pCMV-Δ8.91, and 1.25 µg of pMD.G in 1.25 mL OPTI-MEM and a diluted transfection reagent with 75 µL of transfection reagent in 1.25 mL OPTI-MEM. The DNA mixture was added into the diluted transfection reagent by gently flicking the tube to mix completely, and the transfection mixture was incubated for 20 minutes at room temperature and then added into the cultured cells in a dropwise manner. After 16 hours, the transfection mixture was removed by changing the culture media of 25 mL DMEM supplemented with 10% FBS and 1% BSA. The cultured media containing lentiviruses was harvested at 40 hours post-transfection and replaced with fresh DMEM with 10% FBS and 1% BSA for further harvest. After 24 hours, harvest the cultured media, and the viral harvests were pooled together, and cell debris were removed by centrifugation at 1,250 rpm in 4° C. for 5 minutes. The supernatant was filtered through a 0.45 µm low protein binding membrane and transferred to polypropylene tubes for storage at −80° C.

Pooled CRISPR-Cas9 Genome-Wide Knock-Out N87 Cells Treated with IgG1-AL1-PE38KDELs Immunotoxins-Establishment of Genome-Wide Knock-Out Cell Pools Using the GeCKO v2 Library The Cas9 stably expressing N87 cells were established by transducing lentivirus carrying wild type spCas9 gene, followed by selecting with 5 µg/mL of blasticidin for two weeks. The genome-wide knock-out cell pools were generated by using the GeCKO v2 lentiviral library via spin-infection method. Briefly, $1.2 \times 10^8$ Cas9-expressing N87 cells were plated onto ten 175T cell culture flasks and transduced with lentiviruses expressing GeCKO v2 lenti-Guide library (MOI=0.2), resulting in a transduction efficiency of 20% and approximately 200 cells per lentiGuide construct. Tweeny-four hours post-transduction, cells were then selected with 2.5 µg/mL of puromycin for one week. The puromycin-resistant cells were split with a minimum of $2.4 \times 10^7$ cells per replicate to maintain lentiGuide library complexity.

Pooled CRISPR-Cas9 Genome-Wide Knock-Out N87 Cells Treated with IgG1-AL1-PE38KDELs Immunotoxins-CRISPR-Cas9 Genome-Wide Pooled Screening The genome-wide knock-out N87 cells were plated onto four 175T cell culture flasks with a total cell number of $1 \times 10^7$ cells per culture flask. Immunotoxin IgG1(GH2-20), IgG1(GH2-61) and IgG1(GH2-75) were prepared by pre-incubation of the indicated IgG1 and AL1-PE38KDEL at the molar ratio of 1:1 in serum-free RPMI medium for 1 hour at room temperature. Immunotoxin treatment was performed by incubating the genome-wide knock-out N87 cells with 1 nM of indicated immunotoxin in serum-free RPMI medium at 37° C. Serum-free RPMI medium with AL1-PE38KDEL were used as negative control. After 16 hours of immunotoxin treatment, the immunotoxin was removed by replacing with normal RPMI medium supplemented with 10% FBS. Immunotoxin-treated N87 cells were cultured for an additional 3 days for recovery and then subjected to a second round and third round immunotoxin treatments as mentioned above. After 3 rounds of immunotoxin challenges, the immunotoxin-resistant survivors were collected and expanded to $2.4 \times 10^7$ cells before genomic DNA extraction and analysis.

Pooled CRISPR-Cas9 Genome-Wide Knock-Out N87 Cells Treated with IgG1-AL1-PE38KDELs Immunotoxins-Preparation of Samples for Next Generation Sequencing (NGS)

The NGS sample preparation was performed as a previous publication. Immunotoxin-resistant cells were harvested and the genomic DNA was extracted. The total amount of input genomic DNA (gDNA) for nested PCR was 130 µg for each sample, which achieves a 300× coverage over the whole GECKO v2 lentiGuide library. The first PCR was carried out with 13 separated PCR reactions (with 10 µg gDNA in a 100 µL reaction volume for each PCR) using DNA polymerase. The first PCR amplifications were performed with 18 cycles, and the resulting amplicons were then combined together as the template for the second PCR. Primers used to amplify a region spanning the sgRNA sequences for the first PCR are:

```
F1:
                                        (SEQ ID NO: 24)
5'-AATGGACTATCATATGCTTACCGTAACTTGAAAGTATTTCG-3'

R1:
                                        (SEQ ID NO: 25)
5'-CTTTAGTTTGTATGTCTGTTGCTATTATGTCTACTATTCTTTCC-3'
```

The second PCR was performed to increase the specificity of amplicons, and the barcoded primers with variable nucleotide length in front of barcode were designed for multiplexing of different biological samples and increasing library complexity.

```
F2:
                                        (SEQ ID NO: 26)
5'-(2-6 bp variable length sequence)
(8 bp barcode)CTTGTGGAAAGGACGAAACACCG-3'

R2:
                                        (SEQ ID NO: 27)
5'-(1-5 bp variable length sequence)
TCTACTATTCTTTCCCCTGCACTGT-3'
```

In second PCR reaction, 5 µL of the mixed product from the first PCR was used as template, and the amplification was carried out in a 100 µL volume with 24 cycles. The resulting amplicons from the second PCR were gel extracted, quantified, mixed, and then subjected to NGS analyses.

Pooled CRISPR-Cas9 Genome-Wide Knock-Out N87 Cells Treated with IgG1-AL1-PE38KDELs Immunotoxins-NGS Data Processing and Analysis Sequence reads of CRISPR-Cas9 genome-wide knock-out were produced by high-throughput sequencing. Reads are demultiplexed by sample barcodes. The 20 bp sgRNA from the forward strand of each sequence read is mapped to the designed sgRNA library. Only exactly matched sgRNA reads are counted. Data analysis was performed by MAGeCK using the default parameters. In brief, mapped sgRNA sequences were first quantified by counting the total number of reads and normalization were performed before gene ranking. Those depleted genes in the immunotoxin-resistant pooled CRISPR-Cas9 genome-wide knock-out N87 were identified with false discovery rate (FDR) less than 0.05.

Cytotoxicities of IgG1-AL-PE38KDELs on Gene-Specific Knock-Out N87 Cells-Preparation of KDELR2 or FURIN Gene Knock-Out Cell Pools The Cas9 stably expressing N87 cells were seeded in 6-well culture plates ($2 \times 10^5$ cells per well) one day before lentivirus transduction. Lentiviruses carrying indicated sgRNAs were transduced into the cells by spin-infection method (MOI=1). After 24 hours of lentivirus transduction, cells were selected with 2.5 µg/mL of puromycin for 3 days to remove un-transduced cells. The sequences of the protospacer in each sgRNA are:

```
Control sgRNA:
                                        (SEQ ID NO: 28)
5'-GCGAGGTATTCGGCTCCGCG-3'

KDELR2 sgRNA:
                                        (SEQ ID NO: 29)
5'-CGCCGGCCACCACAGCAATG-3'

FURIN sgRNA:
                                        (SEQ ID NO: 30)
5'-TCGGGGACTATTACCACTTC-3'
```

Cytotoxicities of IgG1-AL-PE38KDELs on Gene-Specific Knock-Out N87 Cells-Cytotoxicity Analysis of KDELR2 or FURIN Knock-Out N87 Cells The KDELR2 or FURIN knock-out N87 cell pools were seeded in 6-well culture plates ($2 \times 10^5$ cells per well) one day before IgG1-AL1-PE38KDEL treatment. Indicated IgGs were pre-incubated with AL1-PE38KDEL at the molar ratio of 1:2 in serum-free RPMI medium for 1 hour at room temperature to form immunotoxins. IgG1-AL1-PE38KDEL treatments were performed in serum-free culture medium with different concentrations at 37° C. for 16 hours, then the culture medium was replaced by fresh RPMI medium with 10% serum for an additional 3 days for culturing at 37° C. The cytotoxicity was assessed using the WST-1 reagent after 72 hours of IgG1-AL1-PE38KDEL treatment.

Statistical Analysis

Data are expressed as mean±SD. Differences between two groups are analyzed using Student's t test, and data set comparisons with statistically significant at P values of <0.05 were labeled with '*' in FIGS. 1-3.

Example 1 Potent Anti-Tumor Activities of the IgG1-Vc-MMAEs in the Xenograft Models The qualities of the ADCs in the form of IgG1-vc-MMAE were assured with in vitro and in vivo assays. The ADCs were prepared with purified IgG1(trastuzumab), IgG1(H32), IgG1(GH2-75), IgG1(GH2-61) and IgG1(GH2-20) conjugated with vc-MMAE to DAR (drug-antibody ratio) of 2 (data not shown). The vc-MMAE conjugation to the IgG1s did not affect the binding affinity of the IgG1s to HER2-ECD, as measured with ELISA ($EC_{50}$ measurements, Table 1), flow cytometry (data not shown) and surface plasmon resonance (SPR) (Table 2). The $EC_{50}$'s determined with ELISA measurements for all the IgG1s and IgG1-vc-MMAEs were similar (Table 1), but in contrast, the flow cytometry measurements indicated that IgG1(GH2-20) and IgG1(GH2-20)-vc-MMAE had lower affinity to cell surface HER2-ECD in comparison with all the other IgG1s and ADCs, most likely due to the close proximity of the epitope of GH2-20 to the cell membrane for which the steric effect was not involved in the ELISA and SPR assay systems. The cytotoxicity ($IC_{50}$) measured with the in vitro cell-based assay for IgG1(trastuzumab)-vc-MMAE, IgG1(H32)-vc-MMAE and IgG1(GH2-61)-vc-MMAE were on the order of 10 nano molar, while the $IC_{50}$ for IgG1(GH2-75)-vc-MMAE and IgG1(GH2-20)-vc-MMAE were on the order of 100 nano molar (Table 3). All the IgG1s and ADCs had similar pharmacokinetic half-life in vivo, as determined with the time courses of the in vivo quantities of the IgG1s and IgG1-vc-MMAEs measured in mice injected with the IgG1s and ADCs (data not shown).

TABLE 1

Binding affinity of specified antibody and HER2-ECD

| IgG1 | EC50 (nM) | IgG1-vc-MMAE | EC50 (nM) |
|---|---|---|---|
| Trastuzumab | 0.049 | IgG1 (trastuzumab)-vc-MMAE | 0.067 |
| IgG1 (H32) | 0.037 | IgG1 (H32)-vc-MMAE | 0.065 |
| IgG1 (GH2-75) | 0.036 | IgG1 (GH2-75)-vc-MMAE | 0.045 |
| IgG1 (GH2-61) | 0.038 | IgG1 (GH2-61)-vc-MMAE | 0.05 |
| IgG1 (GH2-20) | 0.076 | IgG1 (GH2-20)-vc-MMAE | 0.111 |

TABLE 2

Binding affinity and kinetics constants of the IgGs and ADCs determined by SPR

| IgG or ADC | $k_{on}(M^{-1}s^{-1})$ | $k_{off}(s^{-1})$ | $K_D(M)$ | $Chi^2 (RU^2)$ | U-value |
|---|---|---|---|---|---|
| IgG1(trastuzumab) | 1.244E+05 | 6.603E−04 | 5.306E−09 | 0.121 | 1 |
| IgG1(trastuzumab)-vc-MMAE | 1.262E+05 | 6.684E−04 | 5.296E−09 | 0.206 | 3 |
| IgG1(H32) | 8.225E+04 | 3.120E−04 | 3.794E−09 | 0.070 | 3 |
| IgG1(H32)-vc-MMAE | 9.569E+04 | 8.540E−05 | 8.924E−10 | 0.073 | 9 |
| IgG1(GH2-75) | 2.582E+05 | 3.008E−03 | 1.165E−08 | 0.789 | 1 |
| IgG1(GH2-75)-vc-MMAE | 2.779E+05 | 1.655E−03 | 5.956E−09 | 1.920 | 1 |
| IgG1(GH2-61) | 1.863E+05 | 7.144E−04 | 3.835E−09 | 3.710 | 7 |
| IgG1(GH2-61)-vc-MMAE | 2.072E+05 | 1.641E−03 | 7.920E−09 | 0.209 | 2 |
| IgG1(GH2-20) | 2.123E+05 | 5.195E−04 | 2.447E−09 | 5.510 | 20 |
| IgG1(GH2-20)-vc-MMAE | 1.959E+05 | 9.302E−04 | 4.747E−09 | 0.227 | 5 |

$Chi^2$: curve fitting agreement indicator; < threshold of 5.0 is conventionally acceptable.
U-value: an estimate of the uniqueness of the rate constants calculated from the experimental measurements; < threshold of 25 indicates acceptable quantitative determination of the absolute values of the rate constants.

TABLE 3

$IC_{50}$ of specified antibody

| IgG1-vc-MMAE | IC50 (nM) |
|---|---|
| IgG1 (trastuzumab)-vc-MMAE | 27.4 |
| IgG1 (H32)-vc-MMAE | 14.8 |
| IgG1 (GH2-75)-vc-MMAE | 128.5 |
| IgG1 (GH2-61)-vc-MMAE | 46.7 |
| IgG1 (GH2-20)-vc-MMAE | 234 |

Figure 6:
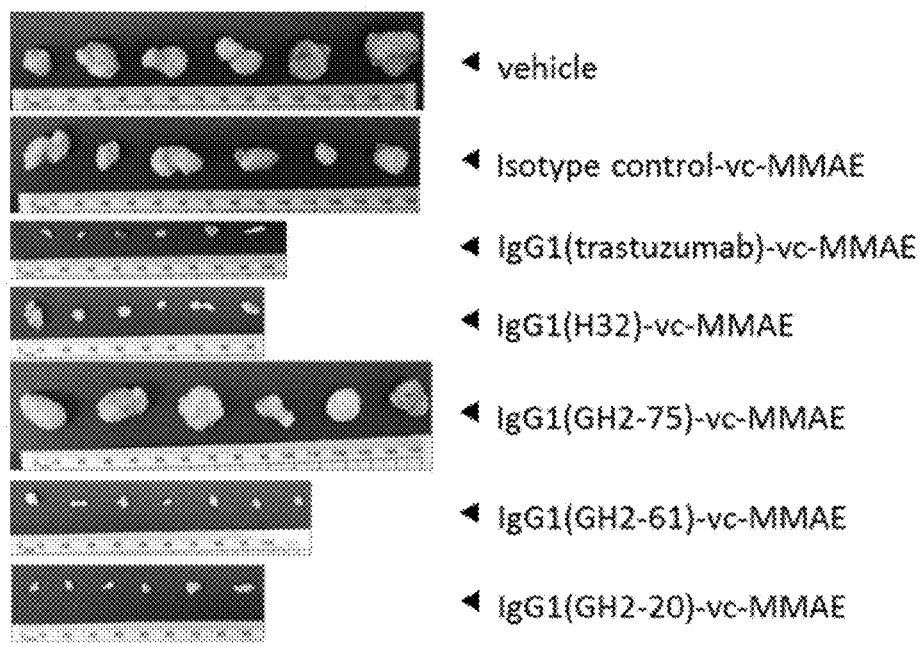
FIG. 6. Excised tumor tissues from control and anti-HER2 IgG1-vc-MMAE-treated mice. At the end point of anti-HER2 IgG1-vc-MMAE treatment (30 mg/kg), tumor xenografts were harvested as shown in the figure.

Xenograft N87 tumors were almost completely eradicated by some of the ADCs at high dosage without signs of off-target toxicity. N87 tumors were implanted to NOD/SCID mice to the size of about 100 mm³ (day 0) and were then treated with ADCs at day 0, day 7 and day 14 at the dosage of 30 mg/kg (FIG. 1, Panels A-C; and FIG. 6). The efficacies of the treatment were ranked as IgG1(GH2-61)-vc-MMAE>IgG1(trastuzumab)-vc-MMAE>IgG1(GH2-20)-vc-MMAE>IgG1(H32)-vc-MMAE>IgG1(GH2-75)-vc-MMAE (FIG. 1, Panels A and B). Photographic depiction of the end point tumors excised from the xenograft models are shown in FIG. 6. All the ADC-treated subjects except those treated with IgG1(GH2-75)-vc-MMAE survived to the end point (day 25) of the experiment (FIG. 1, Panel C), and the ADC treatments almost completely eradicated the xenograft tumors at the end point (FIG. 1, Panel B; and FIG. 6). Serum biochemical analysis of all the subjects at the experiment end point indicated no substantial hepatic or renal toxicity due to the treatment (Table 4), although the IgG1(trastuzumab)-vc-MMAE treated mice had slightly elevated ALP (alkaline phosphatase). ADC-treatments at 10 mg/kg dosage remained effective in preventing tumor progression, with the efficacy ranked as IgG1(H32)-vc-MMAE≈IgG1(GH2-20)-vc-MMAE>IgG1(GH2-61)-vc-MMAE>IgG1(trastuzumab)-vc-MMAE>IgG1(GH2-75)-vc-MMAE (FIG. 1, Panels D and E); the survival curves were similar to those of the high dosage ADC-treatments (FIG. 1, Panel F).

TABLE 4

Effects of anti-HER2 IgG1-vc-MMAEs on serum biochemical parameters in NOD/SCID mice

| | ALT(U/L) | ALP(U/L) | BUN(mg/dL) | CRE(mg/dL) | ALT/ALP |
|---|---|---|---|---|---|
| PBS | 29.33 ± 3.01 | 119.83 ± 35.71 | 21.00 ± 2.35 | 0.63 ± 0.12 | 0.24 |
| IsotypeControl-vc-MMAE | 28.44 ± 9.34 | 102.00 ± 16.52 | 24.49 ± 2.57 | 0.49 ± 0.19 | 0.28 |
| IgG1(trastuzumab)-vc-MMAE | 37.44 ± 14.45 | 184.33 ± 214.99 | 18.70 ± 2.84 | 0.51 ± 0.25 | 0.2 |
| IgG1(H32)-vc-MMAE | 28.44 ± 4.56 | 110.11 ± 11.29 | 21.64 ± 1.45 | 0.52 ± 0.14 | 0.26 |
| IgG1(GH2-75)-vc-MMAE | 45.22 ± 32.97 | 97.00 ± 51.16 | 25.18 ± 5.75 | 0.77 ± 0.20 | 0.47 |

TABLE 4-continued

Effects of anti-HER2 IgG1-vc-MMAEs on serum biochemical parameters in NOD/SCID mice

|  | ALT(U/L) | ALP(U/L) | BUN(mg/dL) | CRE(mg/dL) | ALT/ALP |
|---|---|---|---|---|---|
| IgG1(GH2-61)-vc-MMAE | 25.78 ± 4.92 | 118.33 ± 55.76 | 21.90 ± 2.51 | 0.49 ± 0.25 | 0.22 |
| IgG1(GH2-20)-vc-MMAE | 30.22 ± 7.85 | 101.56 ± 11.19 | 20.80 ± 1.79 | 0.49 ± 0.20 | 0.3 |

End point represents mean ± SD for 6 mice.
ALT (alanine aminotransferase), ALP (alkaline phosphatase), BUN (blood urea nitrogen), CRE (creatinine).

The in vitro efficacy measurements with cultured cells did not always reflect the in vivo efficacies on xenograft models for the ADCs tested. The highly effective in vivo treatments with IgG1(H32)-vc-MMAE, IgG1(trastuzumab)-vc-MMAE and IgG1(GH2-61)-vc-MMAE on xenograft N87 tumors were expected because of the high efficacies measured with cultured N87 cells (Table 3). Similarly, the poor performance of IgG1(GH2-75)-vc-MMAE in treating in vivo tumors reflected consistently with the low efficacy measured in vitro (Table 3). In contrast, it was difficult to reconcile the discrepancy between the in vivo and in vitro efficacies for the IgG1(GH2-20)-vc-MMAE, which was among the ADCs with the best in vivo efficacies and yet had the worst in vitro efficacy among the tested ADCs.

Example 2 Immunotoxins in the Form scFv-PE38KDEL as Surrogates for Detecting Antibody Off-Target Toxicity in Mouse Models To compare the in vivo efficacies of the ADCs with the corresponding immunotoxins scFv-PE38KDEL, the in vivo test of the corresponding scFv-PE38KDELs was performed on the xenograft N87 tumor models. The scFv-PE38KDELs were prepared following the conventional immunotoxin construct. The $EC_{50}$ and $IC_{50}$ of the immunotoxins were measured to assure the qualities of the scFv-PE38KDELs (Tables 5 and 6, respectively).

TABLE 5

Binding affinity of specified immunotoxin

| scFv-PE35KDEL | EC50 (nM) |
|---|---|
| scFv(trastuzumab)-PE38KDEL | 0.15 |
| scFv(H32)-PE38KDEL | 0.08 |
| scFv(GH2-75)-PE38KDEL | 1.31 |
| scFv(GH2-61)-PE38KDEL | 0.53 |
| scFv(GH2-20)-PE38KDEL | 39.08 |

TABLE 6

$IC_{50}$ of specified immunotoxin

| scFv-PE35KDEL | IC50 (pM) |
|---|---|
| scFv(trastuzumab)-PE38KDEL | 3.0 |
| scFv(H32)-PE38KDEL | 3.7 |
| scFv(GH2-75)-PE38KDEL | 7.3 |
| scFv(GH2-61)-PE38KDEL | 16.7 |
| scFv(GH2-20)-PE38KDEL | 33 |

Figure 2:
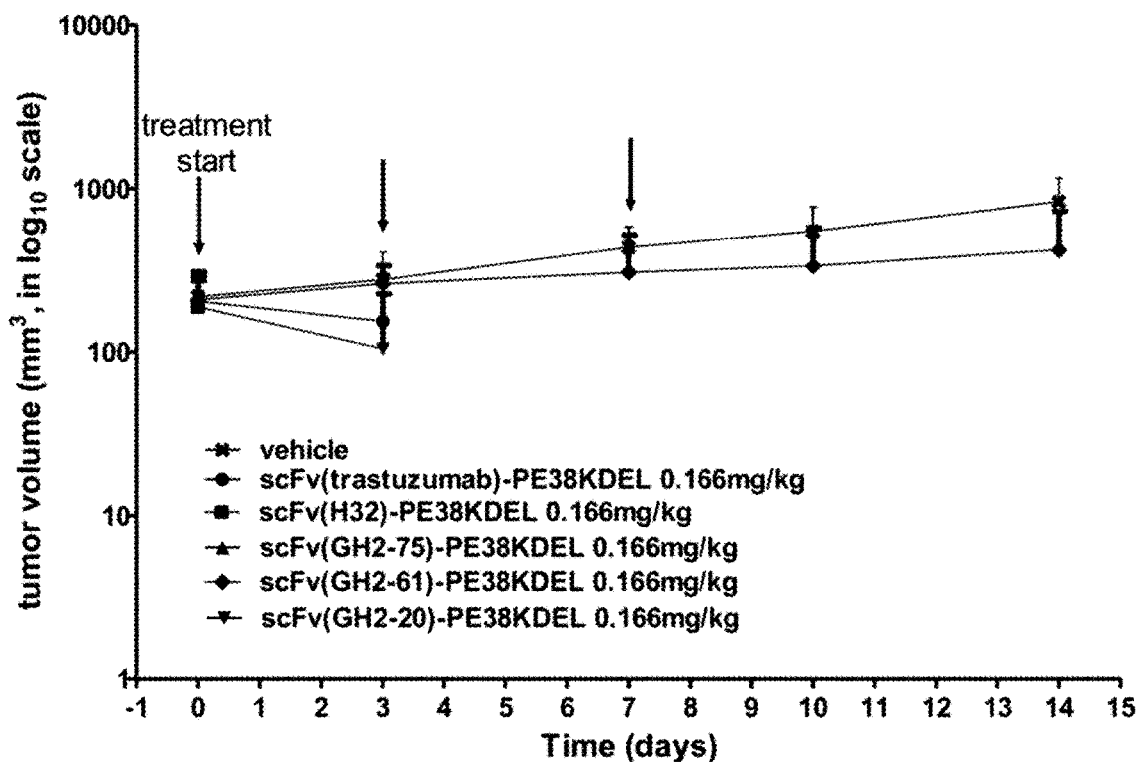
FIG. 2. Treatment of N87 xenograft mouse models with anti-HER2-ECD scFv-PE38KDELs. (Panel A) Data for the time course responses of the tumor size to the scFv-PE38KDEL treatment for xenograft mouse models bearing N87 tumors were attained from the xenograft models randomly assigned into 6 groups (n=5 per group) and treated with 0.166 mg/kg of respective scFv-PE38KDEL at 0, 3 and 7 days as the arrows indicated in this panel. (Panel B) Endpoint tumor volume at day 14 for each of experimental subjects are plotted for each treatment group. Data points for experimental subjects surviving the treatments are shown. (Panel C) Kaplan-Meier survival curves depict the time courses of the fraction of the animal populations surviving the scFv-PE38KDEL treatment.
Figure 2:
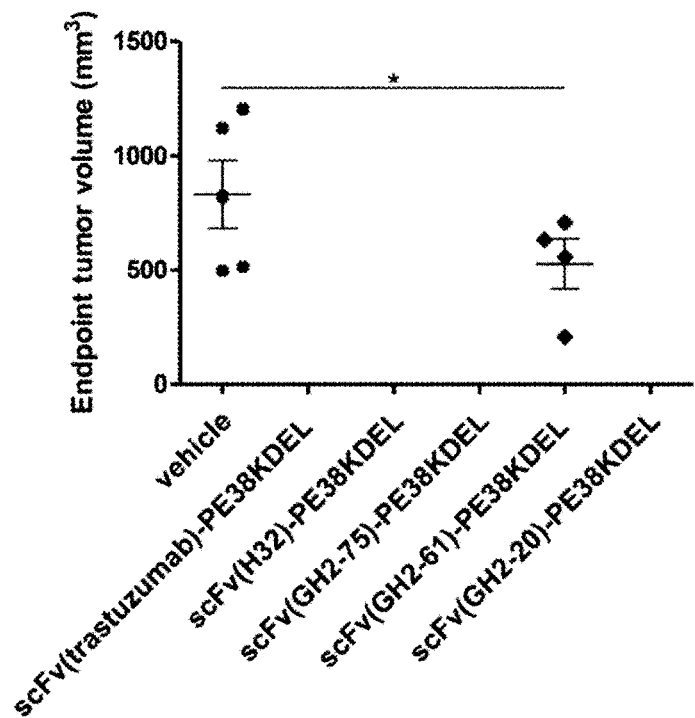
Figure 2:
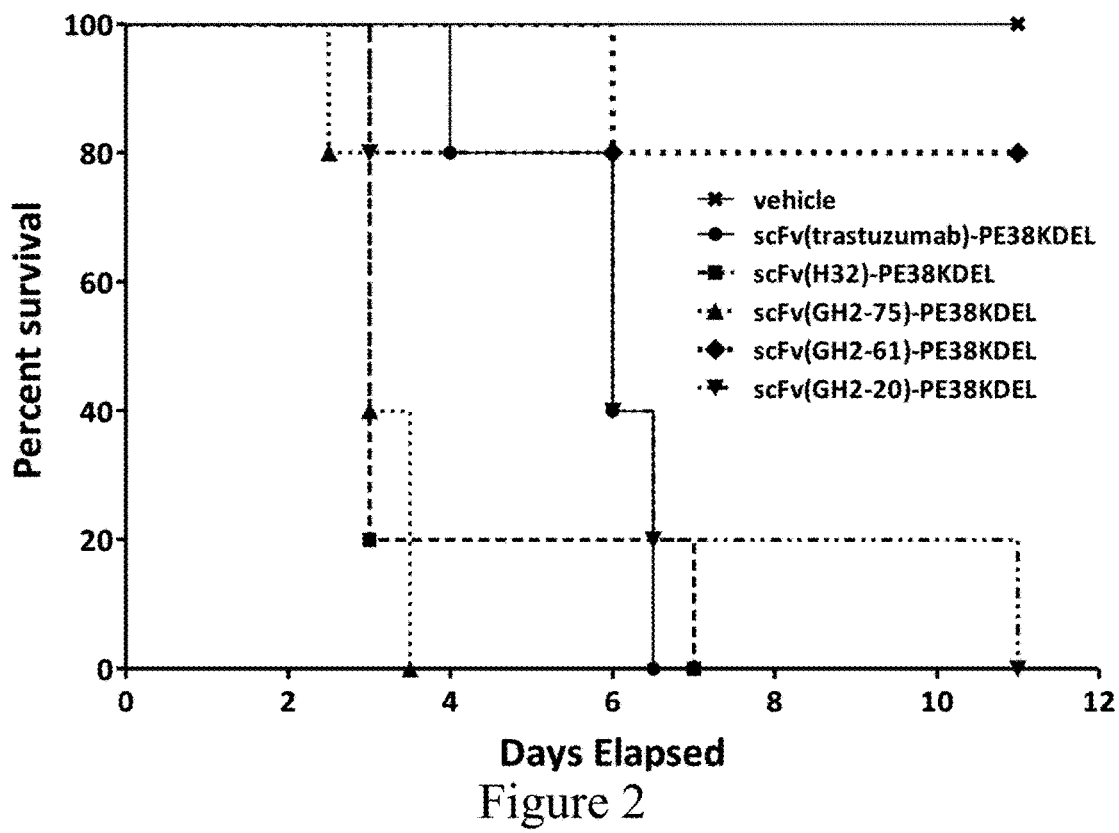

The results of the in vivo tests indicated that the scFv-PE38KDEL immunotoxins were highly toxic to the xenograft models even at very low dosage level (0.166 mg/kg): 80% the scFv(GH2-61)-PE38KDEL-treated xenograft mice survived at the end point of the in vivo experiment (FIG. 2, Panels B and C) with slight benefit in preventing tumor progression (FIG. 2, Panels A and B); all other scFv-PE38KDEL-treated mice did not survive the treatments (FIG. 2, Panel C). The intolerance of the immunotoxins could be resulted from off-target toxicity, and as such, the tolerance of scFv(GH2-61)-PE38KDEL indicated that the IgG1(GH2-61) could have the least off-target propensity among the antibodies tested as the targeting modules for ADCs. Since the off-target toxicity cannot be predicted with the in vitro assay systems, the immunotoxin form scFv-PE38KDEL could be used as a sensitive surrogate system for detecting the antibody's propensity for off-target toxicity in vivo.

Figure 3:
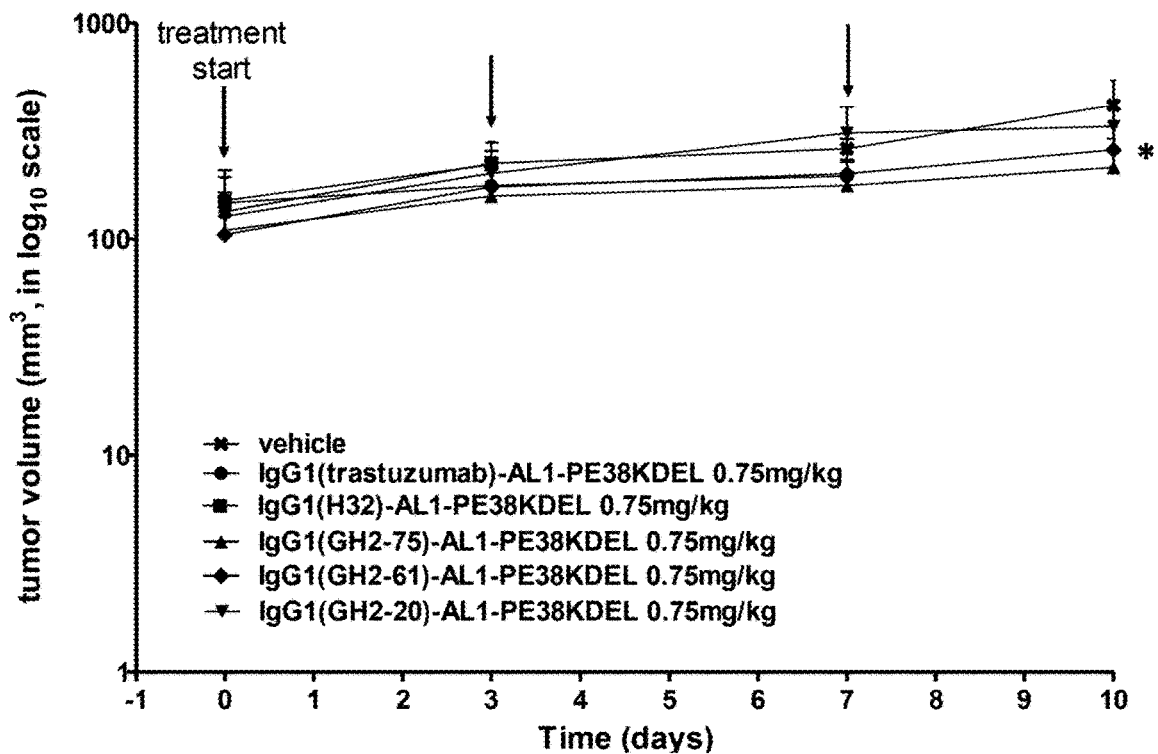
FIG. 3. Treatment of N87 xenograft mouse models with anti-HER2-ECD IgG1-AL1-PE38KDELs. (Panel A) Data for the time course responses of the tumor size to the IgG1-AL1-PE38KDEL treatment for xenograft mouse models bearing N87 tumors were attained from the xenograft models randomly assigned into 6 groups (n=5 per group) and treated (intraperitoneal injection) with 0.75 mg/kg of respective IgG1-AL1-PE38KDEL at 0, 3 and 7 days as the arrows indicated in this panel. (Panel B) Endpoint tumor volume at day 10 for each of experimental subjects are plotted for each treatment group. Data points for experimental subjects surviving the treatments are shown. (Panel C) Kaplan-Meier survival curves depict the time courses of the fraction of the animal populations surviving the IgG1-AL1-PE38KDEL treatment.
Figure 3:
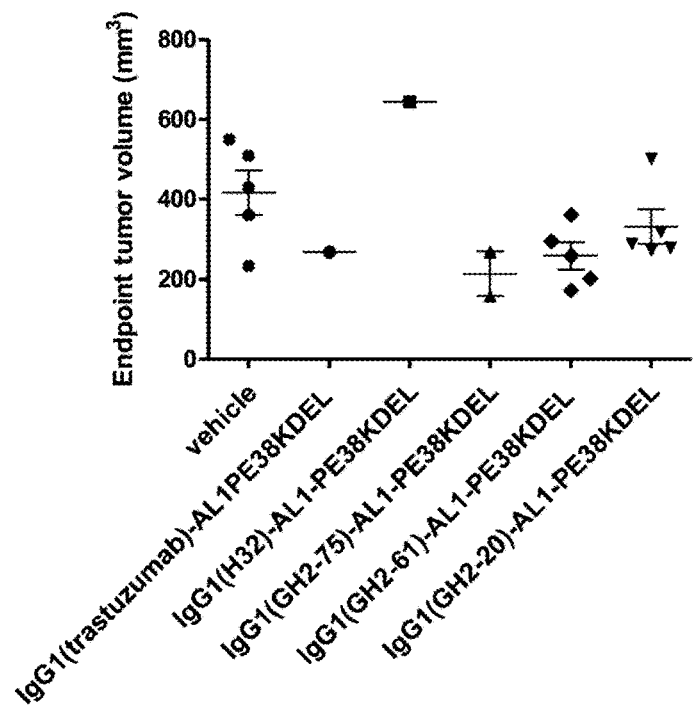
Figure 3:
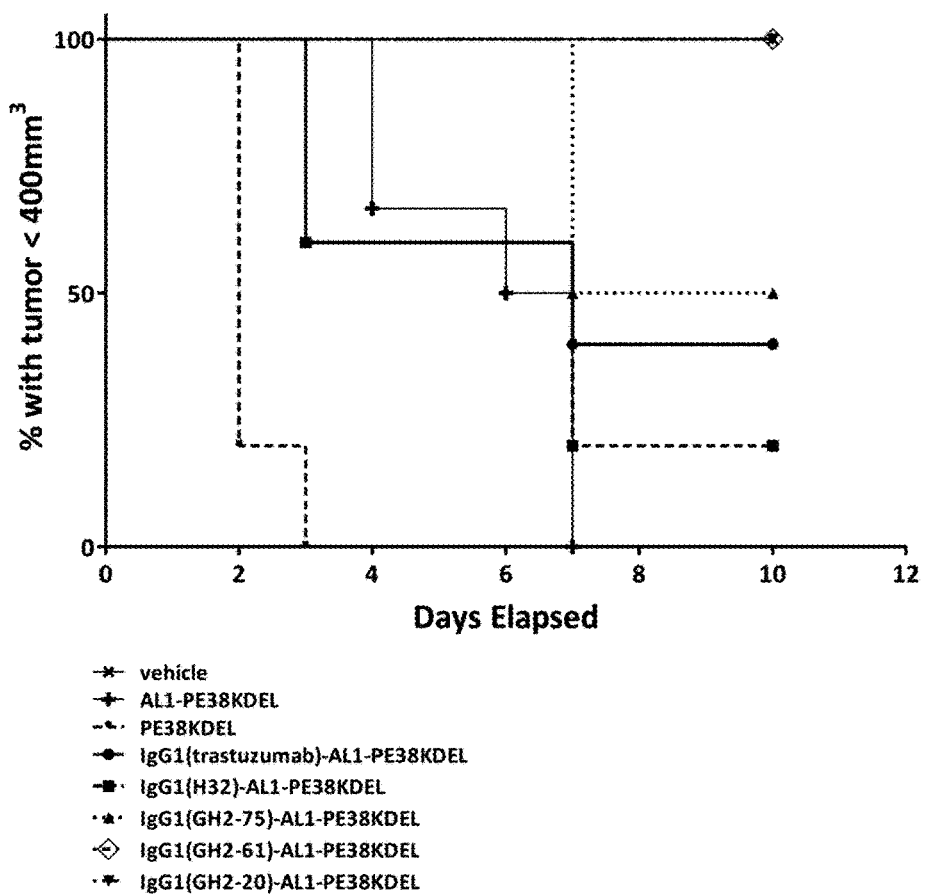

Example 3 IgG1s as Targeting Modules Informed by the Non-Covalently Linked IgG1-AL1-PE38KDEL Immunotoxin Treatments of Xenograft Models As the immunotoxin scFv-PE38KDEL system could inform the off-target toxicity of the antibodies as targeting modules in ADCs, the toxicity of the scFv-PE38KDELs were yet too potent to be measured properly with few test subjects surviving the treatment (FIG. 2). Alternatively, the in vivo test of the non-covalently linked IgG1-AL1-PE38KDEL immunotoxins was performed on the xenograft N87 tumor models to investigate the off-target toxicities and anti-tumor activities of the IgG1s as the targeting modules of the immunoconjugates (FIG. 3). The $IC_{50}$'s of the IgG1-AL1-PE38KDELs were measured in vitro to ensure the qualities of the prepared immunotoxins (Table 7).

TABLE 7

$IC_{50}$ of IgG1-AL1-PE38KDELs

| IgG1-AL1-PE35KDEL | IC50 (pM) |
|---|---|
| scFv(trastuzumab)-AL1-PE35KDEL | 497.7 |
| scFv(H32)-AL1-PE35KDEL | 41.6 |
| scFv(GH2-75)-AL1-PE35KDEL | 36.4 |
| scFv(GH2-61)-AL1-PE35KDEL | 53.9 |
| scFv(GH2-20)-AL1-PE35KDEL | 59.9 |

The results of the in vivo tests indicated that the IgG1-AL1-PE38KDEL immunotoxins were less toxic to the xenograft models at moderate dosage level (<1 mg/kg) (FIG. 3). Still, the mouse models were less tolerant to treatment of IgG1(H32)-AL1-PE38KDEL, IgG1(trastuzumab)-AL1-PE38KDEL and IgG1(GH2-75)-AL1-PE38KDEL (FIG. 3, Panel C), whereas all the test subjects treated with IgG1 (GH2-61)-AL1-PE38KDEL and IgG1(GH2-20)-AL1-PE38KDEL survived the treatment with noticeable efficacies in tumor control (FIG. 3, Panels A and B). The serum biochemical analysis (Table 8) also indicated that the immunotoxins IgG1(H32)-AL1-PE38KDEL, IgG1(trastuzumab)-AL1-PE38KDEL and IgG1(GH2-75)-AL1-PE38KDEL were more toxic than IgG1(GH2-61)-AL1-PE38KDEL and IgG1(GH2-20)-AL1-PE38KDEL, as shown by the substantially elevated serum ALT (alanine aminotransferase) levels (indicating liver toxicity) in the mice treated with the former three immunotoxins. The efficacy trend of the IgG1-AL1-PE38KDELs towards the xenograft models and the toxicity rank as shown in FIG. 3 and Table 8 respectively could be used as a less costly surrogate system to inform the antibody candidates for potent ADCs with less off-target toxicities in vivo.

Together, there was no clear evidence supporting the notion that the anti-HER2-ECD IgG1s tested herein use different pathways of delivering the toxin PE38KDEL, and the gene depletion analysis identified only a subset of the essential genes for the cytotoxicity of PE38KDEL in each set of the immunotoxin-resistant pooled CRISPR-Cas9 genome-wide knock-out N87 cells.

TABLE 8

Effects of anti-HER2 IgG1-AL1-PE38KDELs on serum biochemical parameters in NOD/SCID mice

|  | ALT(U/L) | ALP(U/L) | BUN(mg/dL) | CRE(mg/dL) | ALT/ALP |
|---|---|---|---|---|---|
| PBS | 21.33 ± 2.52 | 225.33 ± 8.14 | 17.67 ± 3.07 | 0.33 ± 0.15 | 0.09 |
| AL-PE38KDEL | 251.67 ± 211.67 | 91.00 ± 11.14 | 18.60 ± 1.18 | 0.70 ± 0.10 | 2.77 |
| IgG1(trastuzumab)-AL1-PE38KDEL | 2908.33 ± 490.42 | 134.00 ± 14.42 | 32.43 ± 1.80 | 0.33 ± 0.23 | 21.7 |
| IgG1(H32)-AL1-PE38KDEL | 583.67 ± 940.42 | 134.33 ± 48.21 | 19.53 ± 2.84 | 0.50 ± 0.26 | 4.34 |
| IgG1(GH2-75)-AL1-PE38KDEL | 898.00 ± 1165.10 | 141.33 ± 63.66 | 25.80 ± 5.15 | 0.53 ± 0.21 | 6.35 |
| IgG1(GH2-61)-AL1-PE38KDEL | 72.00 ± 67.85 | 235.67 ± 36.56 | 19.60 ± 0.78 | 0.63 ± 0.12 | 0.31 |
| IgG1(GH2-20)-AL1-PE38KDEL | 25.33 ± 5.51 | 259.67 ± 68.30 | 20.83 ± 9.17 | 0.73 ± 0.51 | 0.1 |

End point represents meant ± SD for 3 mice.
ALT (alanine aminotransferase), ALP (alkaline phosphatase), BUN (blood urea nitrogen), CRE (creatinine).

Example 4 Mechanism of Cytotoxicity for the IgG1-AL1-PE38KDELs Confirmed with Pooled CRISPR-Cas9 Genome-Wide Knock-Out N87 Cells To address the question if IgG1(GH2-61), IgG1(GH2-20) and IgG1(GH2-75) share the same pathway delivering cytotoxic toxins, the depleted genes in the pooled CRISPR-Cas9 genome-wide knock-out N87 cells that were resistant to the cytotoxicity of the three immunotoxins IgG1(GH2-61)-AL1-PE38KDEL, IgG1(GH2-20)-AL1-PE38KDEL and IgG1(GH2-75)-AL1-PE38KDEL were analyzed (data not shown). The intoxication mechanism of IgG1-AL1-PE38KDEL is anticipated to be initiated by receptor-mediated endocytosis (see the next paragraph). In endosome, peptide linkage in PE38KDEL is cleaved by membrane-bound endoprotease furin. The cleaved toxin trafficked to Golgi binds to KDEL receptor, which subsequently transports the toxin to ER (endoplasmic reticulum), from where the PE38KDEL is transported to cytosol, perhaps through the Sec61 translocon. In cytosol, the PE38 A subunit catalyzes the inactivation of eEF2 (eukaryotic elongation factor 2) by transferring an ADP-ribosyl group from $NAD^+$ to the highly conserved post-translationally modified diphthamide-histidine residue on eEF2. The inactivation of eEF2 arrests the protein synthesis machinery, resulting in apoptosis of the cell. The genes depleted in the immunotoxin-resistant pooled CRISPR-Cas9 genome-wide knock-out N87 cells indicated that the three sets of immunotoxin-resistant cells shared the common depletions of genes involving diphthamide biosynthesis (DPH1~7, DNACJ24 and WDR85), while the IgG1(GH2-20)-AL1-PE38KDEL-resistant N87 cells had additional depletions of genes responsible for PE38KDEL transport among cell compartments. However, N87 cells with FURIN gene knock-out by CRISPR-Cas9 were resistant to all the IgG1-AL1-PE38KDELs (data not shown), indicating that enzymatic cleavage by furin is essential to the cytotoxicity of all the immunotoxins tested herein; N87 cells with KDELR2 gene knock-out were sensitive to all IgG1-AL1-PE38KDELs (data not shown), indicating that KDEL receptor 2 can be circumvented when transporting PE38KDEL to ER.

Figure 4:
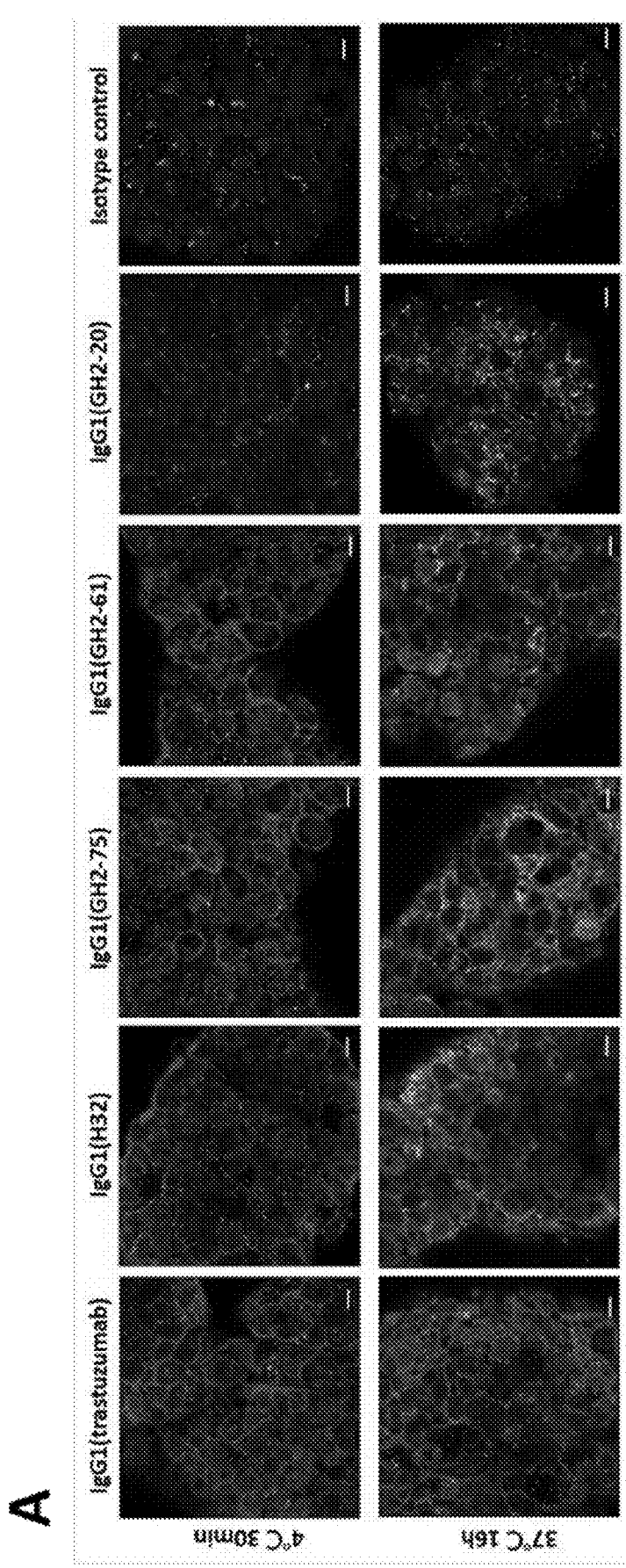
FIG. 4. Internalization of anti-HER2 IgG1s in N87 cells. (Panel A) Confocal microscopy images of N87 cells in the presence of anti-HER2-ECD IgG1s (5 µg/mL concentration for each antibody) were taken 30 min after antibody addition at 4° C. and 16 hours at 37° C. HER2-antibody complexes were stained by Alexa Fluor 633-labeled anti-human antibody (red); lysosomes were stained by anti-human LAMP2 rabbit antibody followed by Alexa Fluor 488-labeled anti-rabbit antibody (green), and nuclei were stained by DAPI (blue). Scale bars: 10 µm. (Panel B) Cellular uptake of $^{111}$In-IgG1 by the $^{111}$In-labeled anti-HER2 IgG1-treated N87 cells are plotted versus incubation time with the antibody; the mean values and standard deviations are calculated with three independent measurements. The details of the experimental procedures in this figure are described in Materials and Methods.
Figure 4:
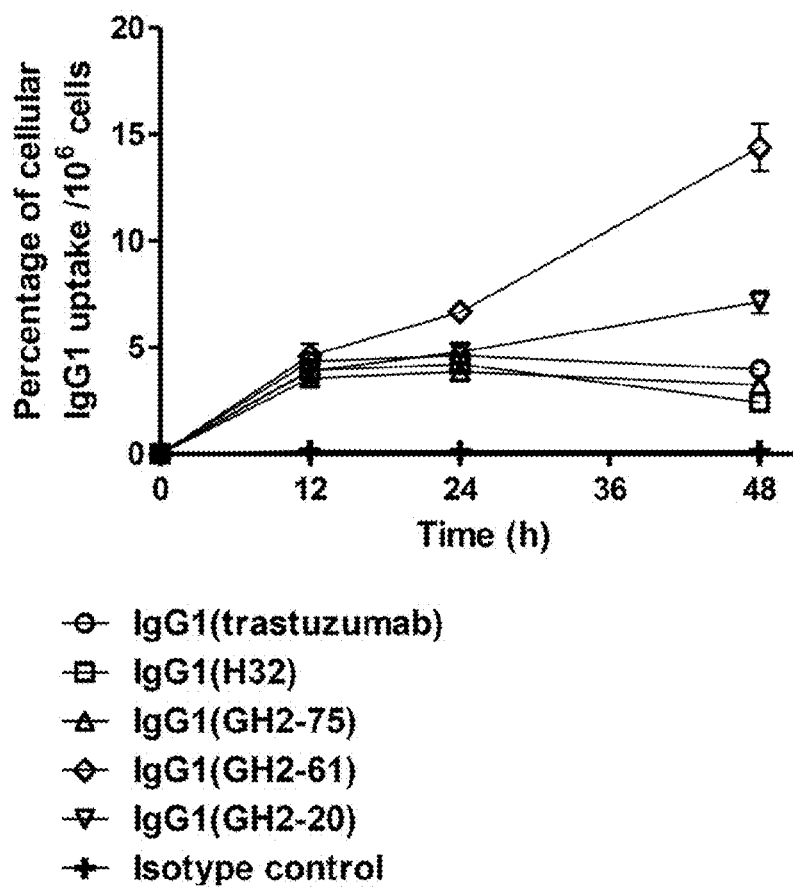
Figure 7:
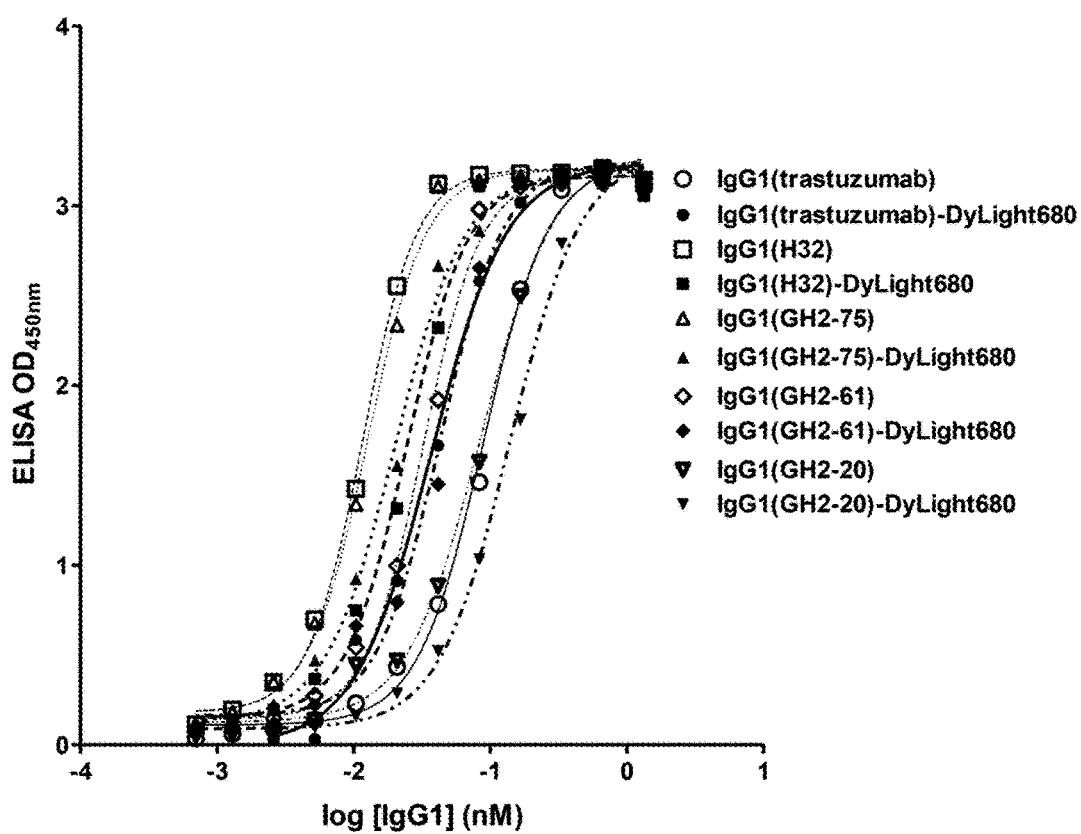
FIG. 7. HER2-ECD binding tests for DyLight 680- or DTPA-labeled anti-HER2 antibodies. (Panel A) Measurements of the HER2-ECD-binding $EC_{50}$'s for DyLight 680-labeled IgG1s are shown in the panel. (Panel B) Measurements of the HER2-ECD-binding $EC_{50}$'s for DTPA-labeled IgG1s are shown in the panel.
Figure 7:
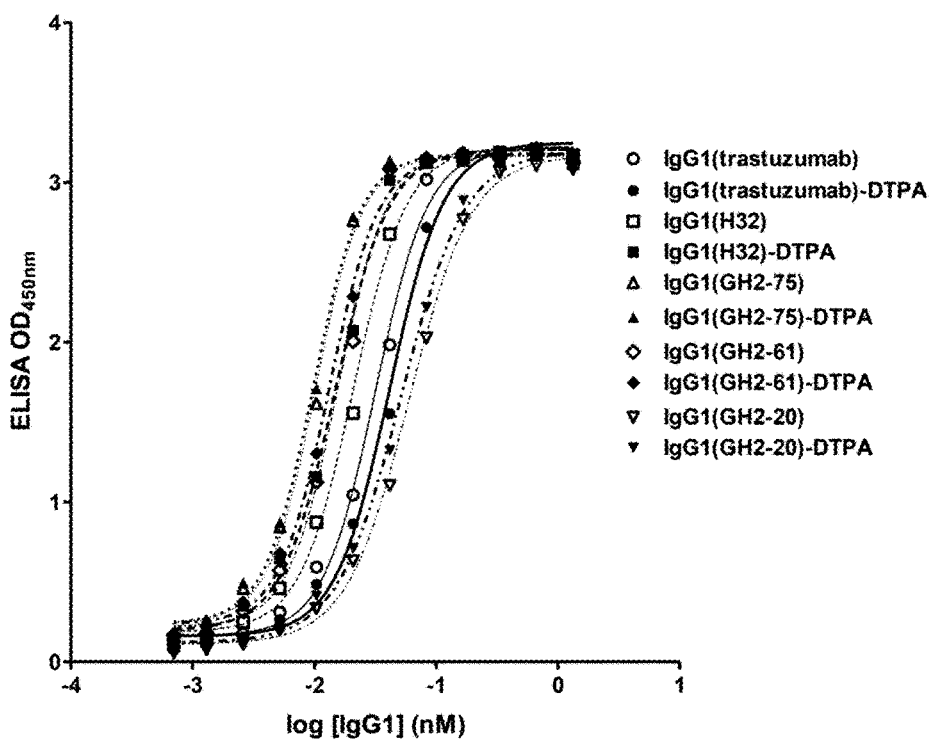

Example 5 Receptor-Mediated Endocytosis of the IgG1s as the Targeting Modules for the Immunoconjugates Cells with no HER2-ECD expressed on cell surface are not sensitive to the immunotoxins with anti-HER-ECD antibodies as targeting modules, suggesting that receptor-mediated endocytosis is essential to initiate the cytotoxicity mechanism of the corresponding immunotoxins. The receptor-mediated endocytosis of the 5 IgG1s was visualized with confocal microscopy before (30 minutes at 4° C. after adding the antibodies) and after (16 hours at 37° C. after adding the antibodies) the antibody endocytosis (FIG. 4, Panel A). IgG1(trastuzumab), IgG1(H32), IgG1(GH2-75) and IgG1(GH2-61) bound to the N87 cell surface and then were internalized. IgG1(GH2-20) had low affinity binding to the HER2-ECD on the cell surface (FIG. 4, Panel A), in agreement with the affinity measurement with flow cytometry (data not shown). Nevertheless, the internalization of IgG1(GH2-20) was clearly visible after 16 hours at 37° C. (FIG. 4, Panel A). Continuous monitoring of the receptor-mediated endocytosis of the IgG1s labelled with radio isotope $^{111}$In, which is in turn chelated to DTPA pre-conjugated on the IgG1 ($EC_{50}$ measurements for the antibodies with/without the conjugated DTPA are shown in FIG. 7, Panel B), further confirmed the internalization of IgG1 (GH2-20) (FIG. 4, Panel B). Two groups of IgG1 internalization patterns are evident in Panel B of FIG. 4: the internalization of IgG1(GH2-20) and IgG1(GH2-61) continued after 24 hours incubation at 37° C., while the internalization of IgG1(GH2-75), IgG1(trastuzumab) and IgG1 (H32) stopped after 24 hours incubation at 37° C. (FIG. 4, Panel B).

One mechanism for the antibody internalization process to stop could be the depletion of the HER2 receptors on the cell surface due to the binding of the antibody; depletion of HER2-ECD on N87 cell surface did occur after incubating IgG1(H32) with the cells (data not shown), explaining only partially as to why the internalization of the IgG1 in the latter group stopped after 24 hours incubation at 37° C. The continuous uptake of the IgG1(GH2-20) and IgG1(GH2-61) by the N87 cells could explain the high potency of the corresponding IgG1-vc-MMAEs and IgG1-AL1-PE38KDELs in treating xenograft N87 tumors (FIGS. 1 and 3).

Example 6 Bio-Distribution of the IgG1s as the Targeting Modules of the Immunoconjugates To gain further insights into the potencies and off-target toxicities of the immunoconjugates, the bio-distribution of the 5 IgG1s was investigated in xenograft models. The 5 IgG1s were conjugated with the fluorescence dye without substantial alteration of their affinities to HER2-ECD (FIG. 7, Panel A). In vivo fluorescence imaging indicated that qualitatively, the IgGs were locally concentrated in the N87 xenograft tumor one day after the administration of the antibodies to the mice (data not shown). Quantitative ex vivo measurements of the bio-distribution indicated that IgG1 (GH2-61) targeted the N87 tumor with the highest local concentration and least off-target propensity (FIG. 5), explaining the high potencies of the corresponding IgG1-vc-MMAEs/IgG1-AL1-PE38KDEL (FIGS. 1 and 3) and the low off-target toxicities of the corresponding scFv-PE38KDEL/IgG1-AL1-PE38KDEL (FIGS. 2 and 3; Table 8). In contrast, the high off-target distribution of IgG1 (trastuzumab) could explain the toxicity of the scFv(trastuzumab)-PE38KDEL and IgG1(trastuzumab)-AL1-PE38KDEL in xenograft models (FIGS. 2 and 3; Tables 2 and 3). MicroSPECT/CT imaging of the IgGs conjugated with radio isotopes $^{111}$In confirmed the specific targeting of the IgG1s to the xenograft N87 tumors. Except for $^{111}$In-IgG1(GH2-75), the tumor (T) uptake increased with time in each group (data not shown). The declined muscle (M) uptake leads to the elevated T/M ratio at 48 hours post-injection, indicating a specific antibody targeting rather than passive diffusion. The difference in T/M ratio between 24 and 48 hours post-injection is a noninvasive index of the antibody internalization rate (data not shown), which is consistent with the high potency of IgG1 (GH2-61) and the low potency of IgG1(GH2-75) as targeting modules in the corresponding ADCs (FIG. 1).

The potency of ADCs as anti-cancer therapeutics requires optimal delivery of the cytotoxic payloads by the ADCs' antibodies as the targeting modules while maintaining low off-target toxicities. Among the three IgG1s (GH2-20, GH2-61 and GH2-75) selected from the general ADC discovery platform, IgG1(GH2-61) and IgG1(GH2-20) were superior candidates to the positive control antibodies (IgG1(H32) and IgG1(trastuzumab)) as the targeting modules for the IgG1-vc-MMAE ADC in terms of both anti-tumor efficacy and off-target toxicity.

Figure 5:
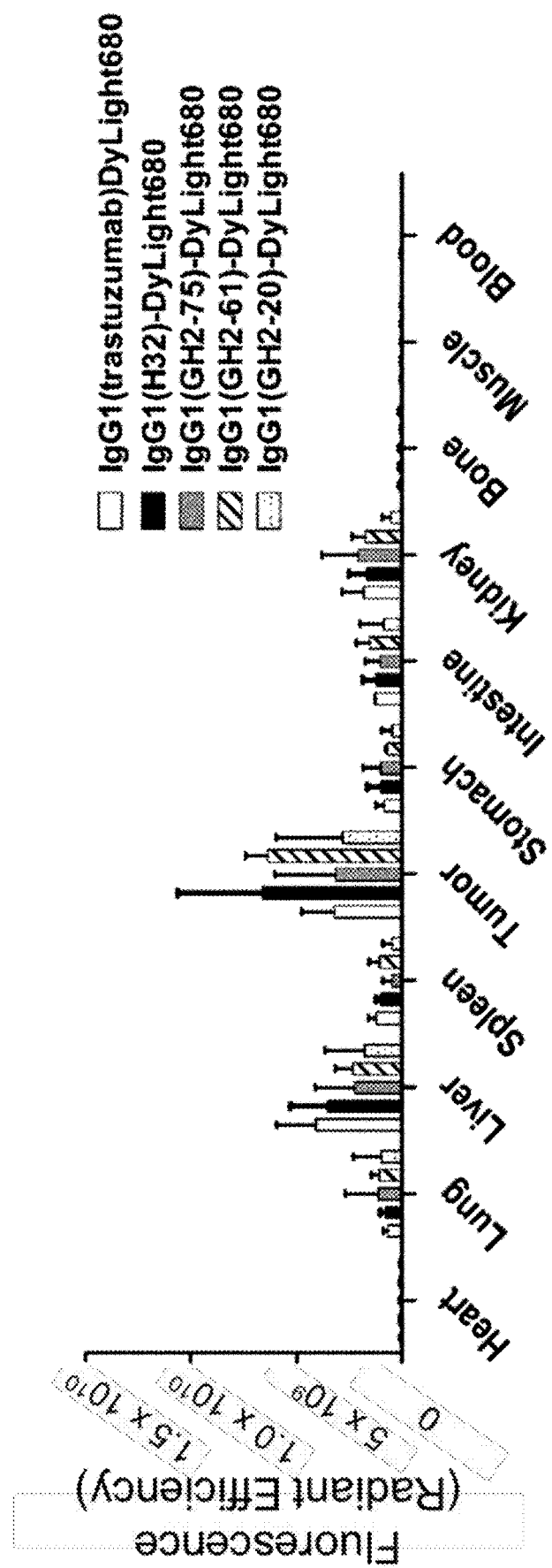
FIG. 5. Bio-distributions of the anti-HER2 IgG1s in N87 xenograft models. Bio-distribution of DyLight 680-labeled anti-HER2 IgG1s in N87 tumor-bearing mice at 24 hours post-injection were determined ex vivo with IVIS. The details of the experimental procedures in this figure are described in Materials and Methods.

The IgG1(GH2-61)-vc-MMAE was comparably potent as the two control ADCs (IgG1(H32)-vc-MMAE and IgG1 (trastuzumab)-vc-MMAE) in treating the xenograft tumor models at 30 mg/kg dosage level, and out-performed the IgG1(trastuzumab)-vc-MMAE at 10 mg/kg dosage level (FIG. 1). The immunotoxins IgG1(GH2-61)-AL1-PE38KDEL and scFv(GH2-61)-PE38KDEL were evidently superior to all other immunotoxins in terms of anti-tumor efficacy and off-target toxicity to the xenograft models (FIGS. 2 and 3). The superior efficacy and toxicity profile of the GH2-61-based immunoconjugates was attributed to efficient internalization of the antibody by the model cultured cells in vitro (FIG. 4, Panel B) and the specific bio-distribution targeting mostly the tumors in the xenograft models in vivo (FIG. 5). In addition, the microSPECT/CT imaging of the IgG1 bio-distribution also supported that the IgG1 (GH2-61) actively targeted the xenograft tumor with superior uptake rate over all the other IgG1 tested (data not shown).

In comparison, IgG1(GH2-20)-vc-MMAE was as potent as IgG1(GH2-61)-vc-MMAE in terms of eradicating xenograft tumors (FIG. 1). IgG1(GH2-20)-AL1-PE38KDEL was comparable to IgG1(GH2-61)-AL1-PE38KDEL in terms of anti-tumor efficacy and off-target toxicity (FIG. 3), as well as sharing the common pathway of delivering the cytotoxic payloads (data not shown), but was more toxic in the form of scFv-PE38KDEL (FIG. 2). However, in contrast to the IgG1(GH2-61), the IgG1(GH2-20) bound to the cell surface HER2-ECD with substantially lower affinity (data not shown), resulting in much higher $IC_{50}$ measured with IgG1-vc-MMAE in vitro (Table 3), slower internalization rate (FIG. 4, Panel B) and less efficient tumor uptake (data not shown). These results indicated that the in vitro and in vivo indirect assays on the antibodies as targeting modules did not necessarily reflect the in vivo efficacies on xenograft models for the immunoconjugates in general.

The off-target toxicities of the immunotoxins could inform the selection of the corresponding ADC candidates. The in vivo mouse models were tolerant to all the HER2-ECD-targeting IgG1-vc-MMAEs at high dosage (FIG. 1 and Table 4). Conversely, the mouse models were intolerant to all the HER2-ECD-targeting scFv-PE38KDELs except scFv (GH2-61)-PE38KDEL at very low dosage (FIG. 2). The intolerance of the immunotoxins could be resulted from off-target toxicity. Since the off-target toxicity cannot be measured or predicted with in vitro systems, the immunotoxin form scFv-PE38KDEL could be used as a sensitive surrogate system for detecting potential off-target toxicity in vivo associated with the antibody as the targeting module. This is particularly useful when the corresponding IgG1-vc-MMAE is not obviously toxic at elevated dosage levels in the experiments with xenograft models. On the other hand, the IgG1-AL1-PE38KDEL immunotoxins were less toxic to the mouse models than the scFv-PE38KDEL immunotoxins at medium dosage (FIG. 3 and Table 8), and the potencies of the IgG1-AL1-PE38KDELs towards the xenograft models could inform those of the corresponding IgG1-vc-MMAEs. Hence, the IgG1-AL1-PE38KDELs could be used as a less costly replacements for the corresponding covalently linked ADCs to identify highly potent antibody candidates with low off-target toxicity. This system could be of particular usefulness when the in vitro efficacy measurements of the immunoconjugates with cultured cells do not reflect their in vivo efficacies on xenograft models.

In summary, antibodies from the synthetic antibody libraries underlying the high throughput immunoconjugate discoveries enabled a rapid process to develop potent ADCs capable of eradicating xenograft tumors in mice, as demonstrated in this work. In vitro assays with cultured cells could narrow the antibody candidate population and gain insights into the optimization of the antibodies as the targeting modules in ADCs, but the in vivo efficacy and toxicity of the ADCs are frequently unpredictable from the in vitro measurements. In vivo experimental measurements with the three forms of immunoconjugates on xenograft models would further inform the ADC candidate selection in terms of potencies and off-target toxicities as anti-cancer therapeutics.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An immunoconjugate that targets a protein antigen, comprising,
   an antibody or a fragment thereof that comprises a heavy chain and a light chain, wherein
   the heavy chain comprises the amino acid sequences of LTINDYG (SEQ ID NO: 1), SIGPSGGFTS (SEQ ID NO: 2) and VIYWGFF (SEQ ID NO: 3), and the light chain comprises the amino acid sequences of NNN, YWTTY (SEQ ID NO: 4) and GSNWPI (SEQ ID NO: 5);
   the heavy chain comprises the amino acid sequences of FTINNWG (SEQ ID NO: 6), GIWPYGGYTY (SEQ ID NO: 7) and YNHHGGV (SEQ ID NO: 8), and the light chain comprises the amino acid sequences of GSN, SWSTS (SEQ ID NO: 9) and YGGWPI (SEQ ID NO: 10); or
   the heavy chain comprises the amino acid sequences of STIGNSG (SEQ ID NO: 11), YIGPYGGYTS (SEQ ID NO: 12) and DDYHWDG (SEQ ID NO: 13), and the light chain comprises the amino acid sequences of SGY, YSS and YYNWPV (SEQ ID NO: 14);
   a functional motif; and
   a linker connecting the functional motif to the antibody or the fragment thereof; wherein
   the functional motif is a drug selected from the group consisting of an immunotoxin, an immunoliposome, and a cytotoxic drug; and the linker is a valine-citrulline dipeptide, a first polypeptide, or an adaptor comprising at least one AL module, wherein each AL module comprises a protein A fragment at the N-terminus, a protein L fragment at the C-terminus, and a second polypeptide connecting the protein A and protein L fragments.

2. The immunoconjugate of claim 1, wherein
the heavy chain comprises the amino acid sequence at least 85% identical to SEQ ID NO: 15, and the light chain comprises the amino acid sequence at least 85% identical to SEQ ID NO: 16;
the heavy chain comprises the amino acid sequence at least 85% identical to SEQ ID NO: 17, and the light chain comprises the amino acid sequence at least 85% identical to SEQ ID NO: 18; or
the heavy chain comprises the amino acid sequence at least 85% identical to SEQ ID NO: 19, and the light chain comprises the amino acid sequence at least 85% identical to SEQ ID NO: 20.

3. The immunoconjugate of claim 1, wherein the protein antigen is human epidermal growth factor receptor 2 (HER2).

4. The immunoconjugate of claim 1, wherein the immunotoxin is an exotoxin.

5. The immunoconjugate of claim 4, wherein the exotoxin is *Pseudomonas* Exotoxin (PE) A or a truncated form of *Pseudomonas* Exotoxin (PE) A, wherein the truncated form of PE A has the amino acid sequence of SEQ ID NO: 32.

6. The immunoconjugate of claim 1, wherein the cytotoxic drug is auristatin or monomethyl auristatin E.

7. The immunoconjugate of claim 6, wherein the cytotoxic drug is monomethyl auristatin E.

8. The immunoconjugate of claim 1, wherein the adaptor comprises the amino acid sequence of SEQ ID NO: 23.

9. A pharmaceutical composition comprising the immunoconjugate of claim 1 and a pharmaceutically acceptable excipient.

10. A method for treating a cancer in a subject, comprising administering to the subject an effective amount of the pharmaceutical composition of claim 9.

11. The method of claim 10, wherein the cancer is selected from the group consisting of gastric cancer, lung cancer, bladder cancer, breast cancer, pancreatic cancer, renal cancer, colorectal cancer, cervical cancer, ovarian cancer, brain tumor, prostate cancer, hepatocellular carcinoma, melanoma, esophageal carcinoma, multiple myeloma, and head and neck squamous cell carcinoma.

12. The method of claim 11, wherein the cancer has HER2 expressed thereon.

13. The method of claim 10, wherein the subject is a human.

* * * * *